US010535134B2

(12) United States Patent
Minai et al.

(10) Patent No.: US 10,535,134 B2
(45) Date of Patent: Jan. 14, 2020

(54) PROCESSING APPARATUS, ENDOSCOPE SYSTEM, ENDOSCOPE APPARATUS, METHOD FOR OPERATING IMAGE PROCESSING APPARATUS, AND COMPUTER-READABLE RECORDING MEDIUM

(71) Applicant: OLYMPUS CORPORATION, Tokyo (JP)

(72) Inventors: Tetsuo Minai, Tokyo (JP); Norio Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 498 days.

(21) Appl. No.: 15/333,365

(22) Filed: Oct. 25, 2016

(65) Prior Publication Data

US 2017/0039710 A1 Feb. 9, 2017

Related U.S. Application Data

(63) Continuation of application No. PCT/JP2015/056911, filed on Mar. 10, 2015.

(30) Foreign Application Priority Data

Jun. 5, 2014 (JP) .................................. 2014-117088

(51) Int. Cl.
*G06T 7/00* (2017.01)
*A61B 1/00* (2006.01)
(Continued)

(52) U.S. Cl.
CPC ........ *G06T 7/0012* (2013.01); *A61B 1/00009* (2013.01); *A61B 1/00016* (2013.01);
(Continued)

(58) Field of Classification Search
CPC ... A61B 1/043; A61B 5/0071; A61B 1/00009; A61B 1/05; A61B 1/06; A61B 1/0638;
(Continued)

(56) References Cited

U.S. PATENT DOCUMENTS

| 5,784,098 A * | 7/1998 | Shoji .................... G01B 11/25 |
| | | 348/139 |
| 6,364,829 B1 * | 4/2002 | Fulghum ............ A61B 1/00009 |
| | | 600/160 |

(Continued)

FOREIGN PATENT DOCUMENTS

| EP | 2127593 A1 * | 12/2009 | ........... A61B 1/0638 |
| EP | 2 366 326 A2 | 9/2011 | |

(Continued)

OTHER PUBLICATIONS

International Search Report dated May 26, 2015 issued in PCT/JP2015/056911.

(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

A processing apparatus processes an image signal generated by pixels that have received light from an object irradiated with first wavelength light. The processing apparatus includes a processor having hardware. The processor is configured to: extract first and second image signals from the image signal of one frame generated by the pixels, the first image signal being generated by a pixel that has received the first wavelength light, the second image signal being generated by a pixel that has received second wavelength light that is fluorescence emitted in response to the first wavelength light; estimate an image signal to be gen- (Continued)

erated by the pixel that has received the second wavelength light, based on the first image signal; and calculate a difference, on a corresponding image signal portion, between the second image signal and the estimated image signal, thereby to obtain a differential image signal.

13 Claims, 19 Drawing Sheets

(51) Int. Cl.
*G02B 23/24* (2006.01)
*A61B 1/04* (2006.01)
*H04N 5/225* (2006.01)
*A61B 1/05* (2006.01)
*A61B 1/06* (2006.01)

(52) U.S. Cl.
CPC .......... *A61B 1/043* (2013.01); *G02B 23/2484* (2013.01); *A61B 1/05* (2013.01); *A61B 1/06* (2013.01); *G06T 2207/10068* (2013.01); *H04N 2005/2255* (2013.01)

(58) Field of Classification Search
CPC ...... G02B 23/2484; G06T 2207/10064; G06T 7/0012; G06T 2207/10068; H04N 7/185; H04N 2005/2255
USPC .......................................................... 600/109
See application file for complete search history.

(56) References Cited

U.S. PATENT DOCUMENTS

| | | | |
|---|---|---|---|
| 7,919,761 B2* | 4/2011 | Ishihara | A61B 1/00009 250/458.1 |
| 2002/0026099 A1* | 2/2002 | Adachi | A61B 1/00009 600/178 |
| 2002/0042556 A1* | 4/2002 | Sugimoto | A61B 1/0638 600/178 |
| 2004/0064016 A1* | 4/2004 | Kobayashi | A61B 1/043 600/109 |
| 2007/0046778 A1* | 3/2007 | Ishihara | A61B 1/00009 348/68 |
| 2009/0137908 A1* | 5/2009 | Patwardhan | A61B 5/0059 600/476 |
| 2010/0036262 A1* | 2/2010 | Watanabe | A61B 1/043 600/478 |
| 2010/0049058 A1* | 2/2010 | Ishihara | A61B 1/043 600/477 |
| 2010/0130818 A1* | 5/2010 | Jung | A61B 1/00006 600/109 |
| 2011/0001061 A1* | 1/2011 | Ishihara | A61B 1/00009 250/458.1 |
| 2011/0117025 A1* | 5/2011 | Dacosta | A61B 5/0059 424/9.6 |
| 2013/0286175 A1 | 10/2013 | Hashimoto et al. | |
| 2014/0128680 A1* | 5/2014 | Shida | A61B 1/043 600/178 |
| 2015/0042774 A1* | 2/2015 | Sugano | H04N 5/2256 348/68 |
| 2017/0148164 A1* | 5/2017 | Totsu | G01N 21/27 |

FOREIGN PATENT DOCUMENTS

| | | | | |
|---|---|---|---|---|
| EP | 2 564 760 A1 | | 3/2013 | |
| JP | 3285265 B2 | | 5/2002 | |
| JP | 2008229026 A | * | 10/2008 | ............. A61B 1/043 |
| JP | 2009-226067 A | | 10/2009 | |
| JP | 2012-005512 A | | 1/2012 | |
| WO | WO 2013/015120 A1 | | 1/2013 | |
| WO | WO 2013/031701 A1 | | 3/2013 | |

OTHER PUBLICATIONS

English Abstract of JP H07-155292 A, dated Jun. 20, 1995, corresponding to JP 3285265 B3.

Extended Supplementary European Search Report dated Jan. 8, 2018 in European Patent Application No. 15 80 2372.1.

* cited by examiner

PROCESSING APPARATUS, ENDOSCOPE SYSTEM, ENDOSCOPE APPARATUS, METHOD FOR OPERATING IMAGE PROCESSING APPARATUS, AND COMPUTER-READABLE RECORDING MEDIUM

CROSS REFERENCES TO RELATED APPLICATIONS

This application is a continuation of PCT international application Ser. No. PCT/JP2015/056911, filed on Mar. 10, 2015 which designates the United States, incorporated herein by reference, and which claims the benefit of priority from Japanese Patent Application No. 2014-117088, filed on Jun. 5, 2014, incorporated herein by reference.

BACKGROUND

1. Technical Field

The disclosure relates to a processing apparatus, an endoscope system, an endoscope apparatus, a method for operating an image processing apparatus, and a computer-readable recording medium, for processing an image signal captured by imaging a biological tissue.

2. Related Art

As a known art in the medical field, an endoscope system is used for observing internal portions of a subject. Typically in the endoscope system, a flexible elongated insertion unit is configured to be inserted into a subject such as a patient, white light as illumination light is emitted from a distal end of the insertion unit, and an imaging unit provided at the distal end of the insertion unit receives reflected light of the white light, thereby to capture an in-vivo image. A biological image captured in this manner is displayed on a display of the endoscope system.

In endoscopic fields in recent years, an endoscope system has appeared that irradiates a biological tissue with excitation light (e.g. blue light) other than white light via an insertion unit inserted into a subject, and receives, by an imaging unit, green autofluorescence emitted from the biological tissue in response to the excitation light, thereby obtaining a fluorescence image signal of the biological tissue (see JP 3285265 B2, for example). This technique utilizes a fact that autofluorescence intensity is weak in an abnormal site such as a lesion site compared with a normal site, and obtains a fluorescence image signal of green autofluorescence emitted from the biological tissue by irradiation with the excitation light. Further in this technique, with a frame different from the fluorescence image signal, an image signal corresponding to reflected light from the biological tissue when irradiated with the green light is obtained as a reference image signal including no autofluorescence of the abnormal site. The reference image signal is then subtracted from the fluorescence image signal to generate a fluorescence differential image signal in which the abnormal site is highlighted and displayed.

SUMMARY

In some embodiments, provided is a processing apparatus for processing an image signal generated by pixels that have received light from an object irradiated with light of a first wavelength band. The processing apparatus includes a processor having hardware. The processor is configured to: extract a first image signal and a second image signal from the image signal of one frame generated by the pixels, the first image signal being generated by a pixel that has received the light of the first wavelength band, the second image signal being generated by a pixel that has received light of a second wavelength band that is fluorescence emitted in response to the light of the first wavelength band; estimate an image signal to be generated by the pixel that has received the light of the second wavelength band, based on the first image signal; and calculate a difference, on a corresponding image signal portion, between the second image signal and the estimated image signal, thereby to obtain a differential image signal.

In some embodiments, an endoscope system includes: a light source configured to emit light of a first wavelength band to an object; an imaging unit configured to receive light from the object irradiated with the light of the first wavelength band to generate an image signal; and a processor having hardware. The processor is configured to: extract a first image signal and a second image signal from the image signal of one frame generated by the imaging unit, the first image signal being generated by a pixel that has received the light of the first wavelength band, the second image signal being generated by a pixel that has received light of a second wavelength band that is fluorescence emitted in response to the light of the first wavelength band; estimate an image signal to be generated by the pixel that has received the light of the second wavelength band, based on the first image signal; and calculate a difference, on a corresponding image signal portion, between the second image signal and the estimated image signal, thereby to obtain a differential image signal.

In some embodiments, provided is a method for operating an image processing apparatus for processing an image signal generated by pixels that have received light from an object irradiated with light of a first wavelength band. The method includes: extracting, from the image signal of one frame generated by the pixels, a first image signal which is generated by a pixel that has received the light of the first wavelength band; estimating an image signal to be generated by a pixel that has received light of a second wavelength band that is fluorescence emitted in response to the light of the first wavelength band, based on the first image signal; extracting, from the image signal of one frame, a second image signal which is generated by the pixel that has received the light of the second wavelength band; and calculating a difference, on a corresponding image signal portion, between the second image signal and the estimated image signal, thereby to obtain a differential image signal.

In some embodiments, provided is a non-transitory computer-readable recording medium with an executable program stored thereon, the program causing a processing apparatus for processing an image signal generated by pixels that have received light from an object irradiated with light of a first wavelength band, to execute: extracting, from the image signal of one frame generated by the pixels, a first image signal which is generated by a pixel that has received the light of the first wavelength band; estimating an image signal to be generated by a pixel that has received light of a second wavelength band that is fluorescence emitted in response to the light of the first wavelength band, based on the first image signal; extracting, from the image signal of one frame, a second image signal which is generated by the pixel that has received the light of the second wavelength band; and calculating a difference, on a corresponding image signal portion, between the second image signal and the estimated image signal, thereby to obtain a differential image signal.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an endoscope system will be described as modes for carrying out the present invention (hereinafter, referred to as embodiment(s)). Note that the present invention is not intended to be limited by these embodiments. The same reference signs are used to designate the same elements throughout the drawings. The drawings are schematic, and the relationship between the thickness and the width of individual members and the ratio between the members are different from an actual case. There are portions having different dimensions and ratios even between the drawings.

First Embodiment

Figure 1:
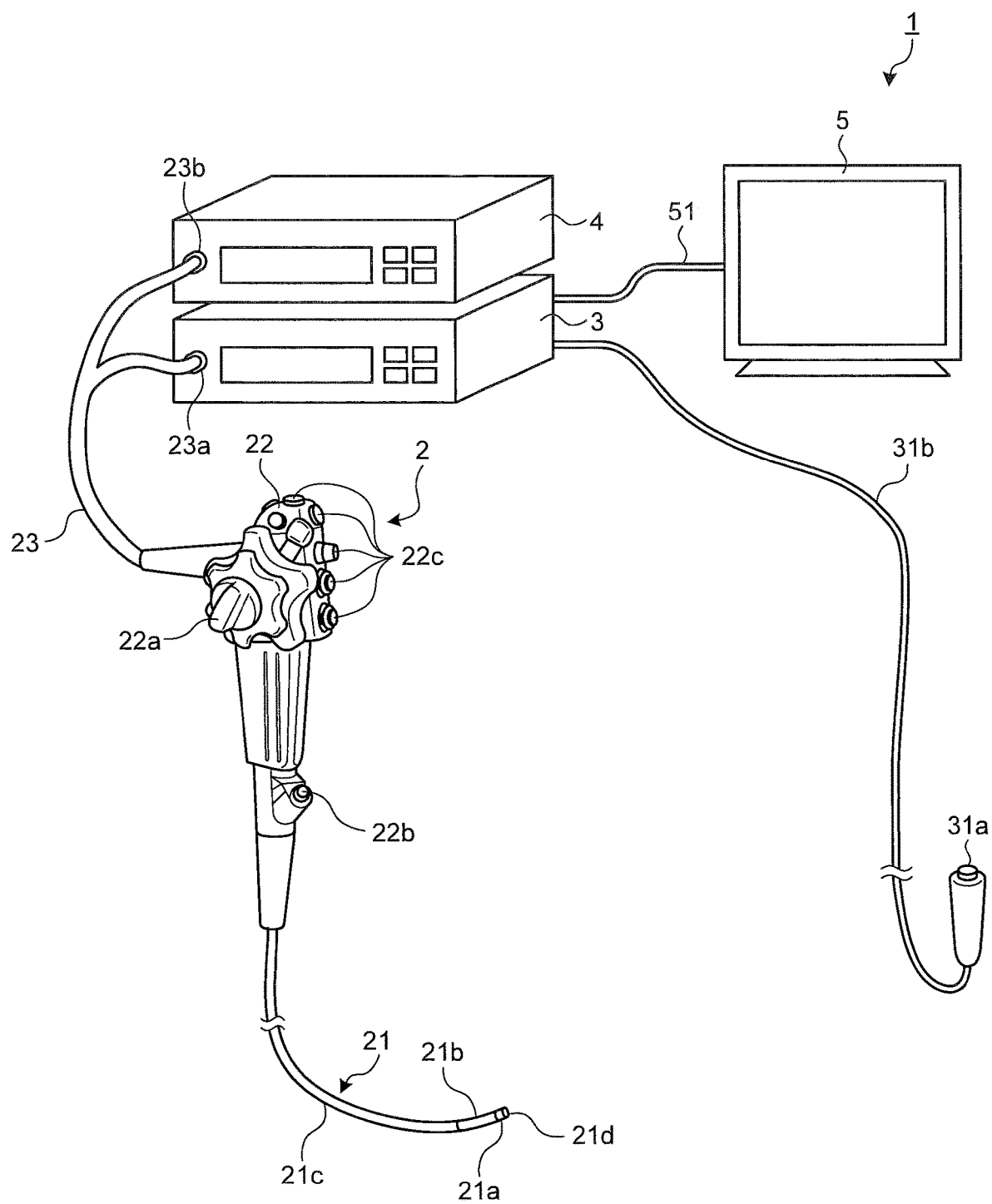
FIG. 1 is a schematic diagram illustrating a general configuration of an endoscope system according to a first embodiment of the present invention.

FIG. 1 is a schematic diagram illustrating a general configuration of an endoscope system according to a first embodiment of the present invention. As illustrated in FIG. 1, an endoscope system 1 according to the first embodiment includes an endoscope 2 (scope), a processing apparatus 3, a light source apparatus 4, and a display device 5. The endoscope 2 (scope) is introduced into a subject, images an internal portion of the subject, and generates an image signal of the internal portion of the subject. The processing apparatus 3 performs predetermined image processing on the image signal captured by the endoscope 2, generates a white light image and a fluorescence differential image in which an abnormal site is highlighted, and controls individual sections of the endoscope system 1. The light source apparatus 4 generates white light as observation light for the endoscope 2 and light for a fluorescence differential image, including fluorescence excitation light. The display device 5 displays an image that corresponds to the image signal on which the processing apparatus 3 has performed image processing.

The endoscope 2 includes an insertion unit 21, an operating unit 22, and a universal cord 23. The insertion unit 21 is inserted into the subject. The operating unit 22 is arranged on a proximal end side of the insertion unit 21 and gripped by an operator. The universal cord 23 has flexibility and extends from the operating unit 22.

The insertion unit 21 includes an illumination fiber (light guide cable) and an electric cable. The insertion unit 21 includes a distal end portion 21a, a bending portion 21b, and a flexible tube portion 21c. The distal end portion 21a includes an imaging unit that incorporates an image sensor to image an internal portion of the subject. The bending portion 21b is a bendable portion formed with a plurality of bending pieces. The flexible tube portion 21c is flexible and provided on a proximal end side of the bending portion 21b. The distal end portion 21a includes an illumination unit, an observation unit, an opening portion 21d, and an air/water feeding nozzle (not illustrated). The illumination unit illuminates an inside of the subject via an illumination lens. The observation unit images the inside of the subject. The opening portion 21d communicates with a treatment tool channel.

The operating unit 22 includes a bending knob 22a, a treatment tool insertion section 22b, and a plurality of switching sections 22c. The bending knob 22a is used to bend the bending portion 21b in up-down and left-right directions. The treatment tool insertion section 22b is a section through which a treatment tool such as biological forceps and a laser knife is inserted into the body cavity of the subject. Each of the switching sections 22c is used to operate peripheral equipment such as the processing apparatus 3, the light source apparatus 4, an air feeding apparatus, a water feeding apparatus, and a gas feeding apparatus. A treatment tool inserted from the treatment tool insertion section 22b passes through an internal treatment tool channel and comes out from the opening portion 21d of the distal end of the insertion unit 21.

The universal cord 23 includes an illumination fiber and an electric cable. The universal cord 23 is branched at a proximal end. One end portion of the branched section is a connector 23b, and the other proximal end is a connector 23a. The connector 23a is removably attached to the processing apparatus 3. The connector 23b is removably attached to the light source apparatus 4. The universal cord 23 transmits illumination light emitted from the light source apparatus 4 to the distal end portion 21a via the connector 23b, the operating unit 22, and the flexible tube portion 21c. The universal cord 23 transmits an image signal captured by the imaging unit provided at the distal end portion 21a, to the processing apparatus 3.

The processing apparatus 3 performs predetermined image processing on an image signal inside the subject, captured by the imaging unit at the distal end portion 21a of the endoscope 2. The processing apparatus 3 generates a white light image, and a fluorescence differential image in which an abnormal site is highlighted. The processing apparatus 3 controls individual sections of the endoscope system 1 based on various instruction signals transmitted from the switching section 22c on the operating unit 22 of the endoscope 2, via the universal cord 23. The processing apparatus 3 includes, as a portion of the input unit, a changeover switch 31a including a remote switch such as a pull switch. A signal that indicates the start of generation of a fluorescence differential image is input from the changeover switch 31a into the processing apparatus 3 via a cord 31b.

The light source apparatus 4 includes a white light source, a light source for a differential image, and a condenser lens. The white light source emits white light. The light source for a differential image emits light for a fluorescence differential image (light of the first wavelength band), including fluorescence excitation light. Under the processing apparatus 3, the light source apparatus 4 emits white light from the white light source and supplies the white light to the endoscope 2 connected via the connector 23b and the illumination fiber of the universal cord 23, as illumination light to the internal portion of the subject, as an object. When the signal that indicates the start of generation of a fluorescence differential image is input into the processing apparatus 3, the light source apparatus 4 emits light for a fluorescence differential image from the light source for a differential image under the control of the processing apparatus 3, and supplies the light to the endoscope 2. When the biological tissue inside the subject as an object is irradiated with the light for a fluorescence differential image, the biological tissue emits autofluorescence in response to the light. The autofluorescence is light of a second wavelength band different from the first wavelength band.

The display device 5 includes a display using liquid crystal or organic electro luminescence (EL). The display device 5 displays, via a video cable 51, various information including an image that corresponds to a display image signal that has undergone predetermined image processing performed by the processing apparatus 3. With this configuration, the operator can observe a desired position inside the subject and judge conditions by operating the endoscope 2 while viewing an image (in-vivo image) displayed by the display device 5.

Figure 2:
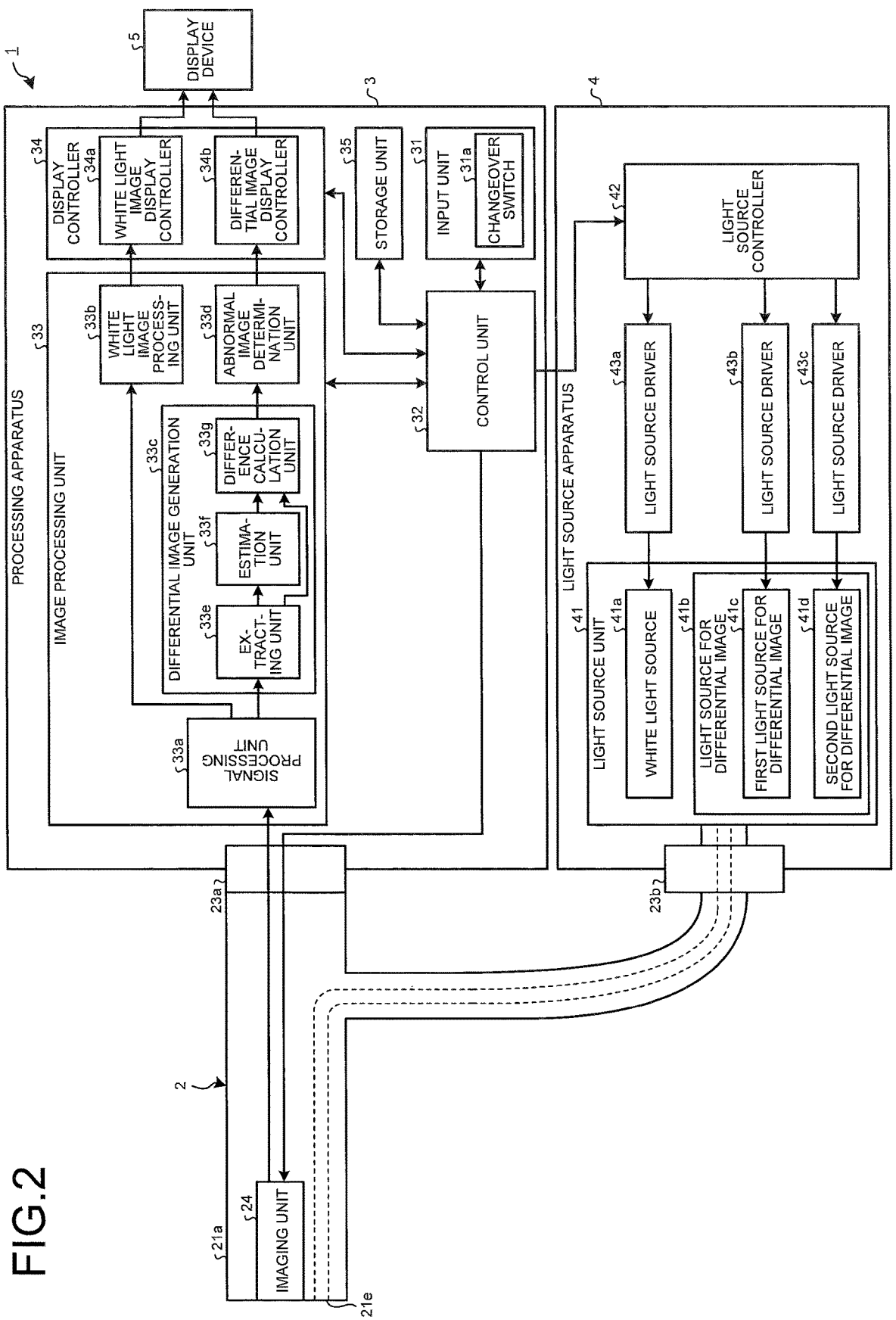
FIG. 2 is a block diagram schematically illustrating a configuration of an endoscope system illustrated in FIG. 1.

Next, reference will be made to configurations of the endoscope 2, the processing apparatus 3, and the light source apparatus 4, illustrated in FIG. 1. FIG. 2 is a block diagram schematically illustrating a configuration of the endoscope system 1.

The endoscope 2 includes an imaging unit 24 at the distal end portion 21a. The imaging unit 24 includes an optical system and an image sensor having a plurality of pixels. An exemplary image sensor is a CCD image sensor, or a CMOS image sensor. On a light receiving plane of the image sensor, a plurality of pixels that receives light from the object and photoelectrically converts the received light to generate an image signal is arranged in a matrix. The image sensor of the imaging unit 24 includes a blue (B) pixel, a green (G) pixel, and a red (R) pixel. An optical system including an objective lens for forming an optical image on a light receiving plane of the image sensor is arranged on a light receiving plane side of the image sensor. The plurality of pixels of the imaging unit 24 generates an image signal representing an internal portion of the subject as an object, from the optical image formed on the light receiving plane, according to the control by a control unit 32 of the processing apparatus 3. The image signal generated by the plurality of pixels is output to the processing apparatus 3 via a cable (not illustrated) and the connector 23a.

Next, the processing apparatus 3 will be described. The processing apparatus 3 includes an input unit 31, the control unit 32, an image processing unit 33, a display controller 34, and a storage unit 35.

The input unit 31 includes an operation device such as a mouse, keyboard, and a touch panel, and receives input of various instruction information of the endoscope system 1. Specifically, the input unit 31 receives various instruction information including subject information (for example, ID, date of birth, and name), identification information of the endoscope 2 (for example, ID and inspection items), and details of inspection. The input unit 31 includes the above-described changeover switch 31a and receives input of a signal that indicates the start of generation of a fluorescence differential image.

The control unit 32 includes a CPU. The control unit 32 controls processing operation of individual sections of the processing apparatus 3. The control unit 32 controls operation of the processing apparatus 3 by performing transfer, or the like, of instruction information or data toward individual components of the processing apparatus 3. The control unit 32 is connected, via individual cables, to individual components of the imaging unit 24 and the light source apparatus 4, and controls operation of the imaging unit 24 and the light source apparatus 4. In a case where the control unit 32 has received from the input unit 31 input of a signal that indicates the start of generation of a fluorescence differential image, the control unit 32 controls the light source apparatus 4 to switch from irradiation with white light to irradiation with light for a fluorescence differential image.

Under control of the control unit 32, the image processing unit 33 performs predetermined signal processing on the image signal generated by the imaging unit 24. The image processing unit 33 includes a signal processing unit 33a, a white light image processing unit 33b, a differential image generation unit 33c, and an abnormal image determination unit 33d (determination unit).

Under the control of the control unit 32, the signal processing unit 33a performs signal processing including optical black subtraction processing, gain adjustment processing, synchronization processing of an image signal, gamma correction processing, on the image signal output from the imaging unit 24. In a case where the image signal as a processing target is a white light image signal captured by imaging the object irradiated with the white light, the signal processing unit 33a executes individual signal processing under the conditions corresponding to the white light image, and outputs the image signal after signal processing, onto the white light image processing unit 33b. In a case where the image signal as a processing target is an image signal for fluorescence differential image generation, captured by imaging the object irradiated with the light for a fluorescence differential image, the signal processing unit 33a executes signal processing under the conditions corresponding to the image signal for fluorescence differential image generation, and outputs the image signal after signal processing, onto the differential image generation unit 33c.

The white light image processing unit 33b performs image processing for white light image signal, such as white balance (WB) adjustment processing, color matrix computing processing, color reproduction processing, and edge emphasis processing, on the white light image signal output from the signal processing unit 33a.

The differential image generation unit 33c generates a fluorescence differential image signal in which an abnormal site is highlighted, by performing predetermined image processing on the image signal for fluorescence differential image generation, output from the signal processing unit 33a. The differential image generation unit 33c includes an extracting unit 33e, an estimation unit 33f, and a difference calculation unit 33g (calculation unit).

The extracting unit 33e extracts a first image signal and a second image signal from the image signal of one frame generated by the plurality of pixels of the imaging unit 24. The first image signal is an image signal generated by a pixel that has received light of the first wavelength band. The second image signal is an image signal generated by a pixel that has received light of the second wavelength band.

Based on the first image signal extracted by the extracting unit 33e, the estimation unit 33f performs calculation processing that estimates the image signal to be generated by the pixel that has received the light of the second wavelength band.

The difference calculation unit 33g employs the image signal estimated by the estimation unit 33f (estimated image signal), as a reference image signal. The difference calculation unit 33g calculates a difference, on a corresponding image portion, between the second image signal extracted by the extracting unit 33e and the estimated image signal estimated by the estimation unit 33f, and thereby generates a fluorescence differential image signal.

The abnormal image determination unit 33d determines a fluorescence differential image signal that includes an image portion having a differential value that exceeds a predetermined value among the fluorescence differential image signal calculated by the difference calculation unit 33g, as an abnormal image including an abnormal site. The abnormal image determination unit 33d uses absolute values for the differential value and the predetermined value and determines a fluorescence differential image signal that includes an image portion having a differential value that exceeds a predetermined value, as an abnormal image including an abnormal site. The predetermined value is set, for example, based on a previously-obtained image signal of a pixel that has received autofluorescence emitted from an abnormal site and a previously-obtained image signal of a pixel that has received reflected light from a biological tissue when irradiated with light having a wavelength band equal to the wavelength band of fluorescence. The image portion having a differential value larger than the predetermined value can be determined as an abnormal site. The image portion having a differential value smaller than the predetermined value can be determined as a normal site. The abnormal image determination unit 33d sets an abnormal flag toward the fluorescence differential image signal determined as an abnormal image.

The display controller 34 generates a display image signal to be displayed on the display device 5, from the image signal processed by the image processing unit 33. The display controller 34 converts the display image signal from a digital signal to an analog signal, changes the converted analog image signal into a format of high-vision system, or the like, and then, outputs the signal to the display device 5. The display controller 34 includes a white light image display controller 34a and a differential image display controller 34b. The white light image display controller 34a converts a white light image signal output by the white light image processing unit 33b, into a display white light image signal.

The differential image display controller 34b generates a differential image display image signal in which an image portion (abnormal site) having a differential value that exceeds the above-described predetermined value is displayed in a color distinguishable from other portion (normal site) for the fluorescence differential image signal output from the abnormal image determination unit 33d after calculation by the difference calculation unit 33g. The color used to indicate the abnormal site can be any color as long as it is distinguishable from normal sites.

The storage unit 35 includes volatile memory and a non-volatile memory, and stores various programs for operating the processing apparatus 3 and the light source apparatus 4. The storage unit 35 temporarily stores information being processed by the processing apparatus 3. The storage unit 35 stores, in a unit of frame, the image signal captured by the imaging unit 24. The storage unit 35 stores the white light image signal and the fluorescence differential image signal, generated by the image processing unit 33. The storage unit 35 may be formed with a memory card, or the like, attached from outside of the processing apparatus 3.

Next, the light source apparatus 4 will be described. The light source apparatus 4 includes a light source unit 41, a light source controller 42, and light source drivers 43a to 43c.

The light source unit 41 includes various light sources and an optical system such as a condenser lens. The light source unit 41 includes a white light source 41a and a light source 41b for differential image. The white light source 41a includes a white light LED, or the like. The light source 41b for differential image emits light for a fluorescence differential image, namely, the light of the first wavelength band. The light source 41b for differential image includes a first light source 41c for differential image and a second light source 41d for differential image. The first light source 41c for differential image includes an LED that emits light $E_b$ having a wavelength of 390 nm to 470 nm, namely, fluorescence excitation light. The second light source 41d for differential image includes an LED that emits light $E_r$ having a wavelength of 650 nm to 800 nm.

Based on the control by the control unit 32 of the processing apparatus 3, the light source controller 42 controls light emission operation of the light source unit 41 by controlling power supply performed on the light source drivers 43a to 43c. Under the control by the control unit 32, the light source controller 42 controls switching between irradiation with white light and irradiation with light including fluorescence excitation light.

Under the control by the light source controller 42, the light source driver 43a supplies predetermined power to the white light source 41a. Under the control by the light source controller 42, the light source driver 43b supplies predetermined power to the first light source 41c for differential image. Under the control by the light source controller 42, the light source driver 43c supplies predetermined power to the second light source 41d for differential image. With this configuration, the object is illuminated with the light emitted from the white light source 41a, the first light source 41c for differential image, and the second light source 41d for differential image from an illumination window 21e on the distal end portion 21a of the insertion unit 21 via the connector 23b and the universal cord 23. The imaging unit 24 is arranged in the vicinity of the illumination window 21e.

Figure 3A:
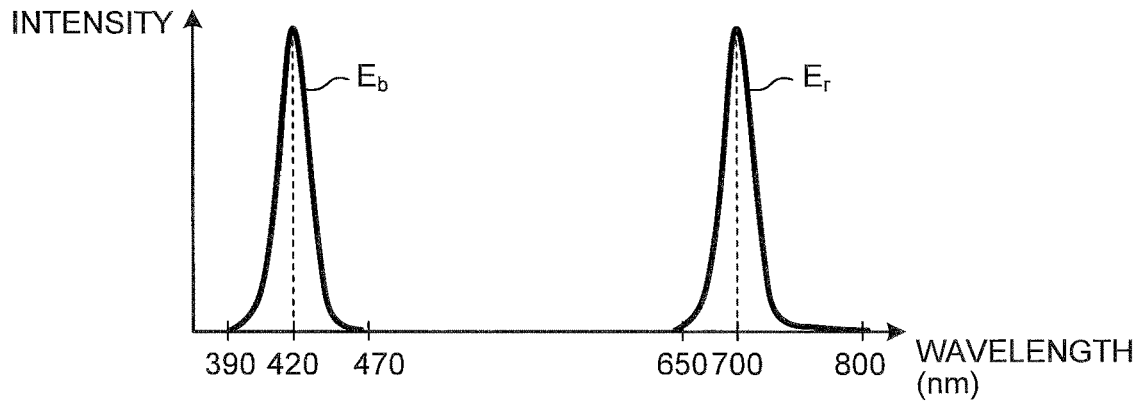
FIG. 3A is a diagram illustrating wavelength dependency of spectral characteristics of a light source for a differential image, according to an embodiment.

FIG. 3A is a diagram illustrating wavelength dependency of spectral characteristics of the light source for a differential image, according to the first embodiment. As light for a fluorescence differential image (light of the first wavelength band), the light source 41b for differential image emits light $E_b$, which is fluorescence excitation light, and the light $E_r$. The light $E_b$ is narrowband light having a spectrum with a wavelength band of 390 nm to 470 nm and a peak wavelength of 420 nm. The light $E_r$ is narrowband light having a spectrum with a wavelength band of 650 nm to 800 nm and a peak wavelength of 700 nm. When a biological tissue inside the subject as an object is irradiated with the light $E_b$ having a wavelength of 390 nm to 470 nm, the biological tissue emits autofluorescence in response to the light $E_b$.

Figure 3B:
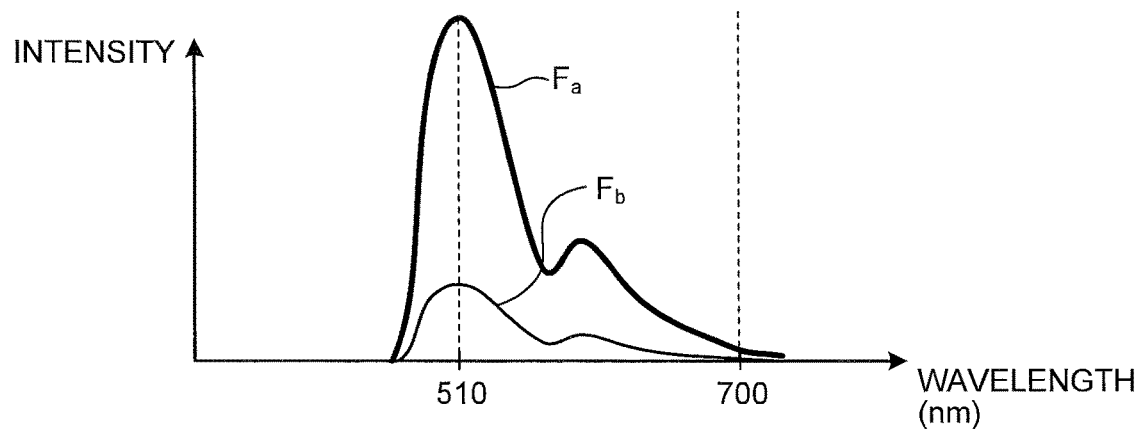
FIG. 3B is a diagram illustrating spectral characteristics of autofluorescence of a biological tissue, according to an embodiment.

FIG. 3B is a diagram illustrating spectral characteristics of autofluorescence at a mucosal tissue among the biological tissues, specifically illustrating spectral characteristics of autofluorescence in a normal site and an abnormal site superposed with each other. Note that, intensity of autofluorescence emitted from the biological tissue in practice is approximately 0.01 times of the intensity of the fluorescence excitation light, and thus, FIG. 3B indicates intensity of autofluorescence in a scale different from the scale in FIG. 3A.

As illustrated in FIG. 3B, this autofluorescence has a wavelength distribution different from the wavelength distribution of the light of the first wavelength band regardless of abnormal/normal sites, with its peak wavelength being 510 nm, having intensity mainly in the wavelength of 500 nm to 600 nm (second wavelength band). This autofluorescence also has a second peak around 660 nm. In any of wavelength components, normal-site autofluorescence $F_a$ and abnormal-site autofluorescence $F_b$ have different intensities, that is, autofluorescence intensity is lower in an abnormal site having a lesion, or the like, than in a normal site.

Figure 3C:
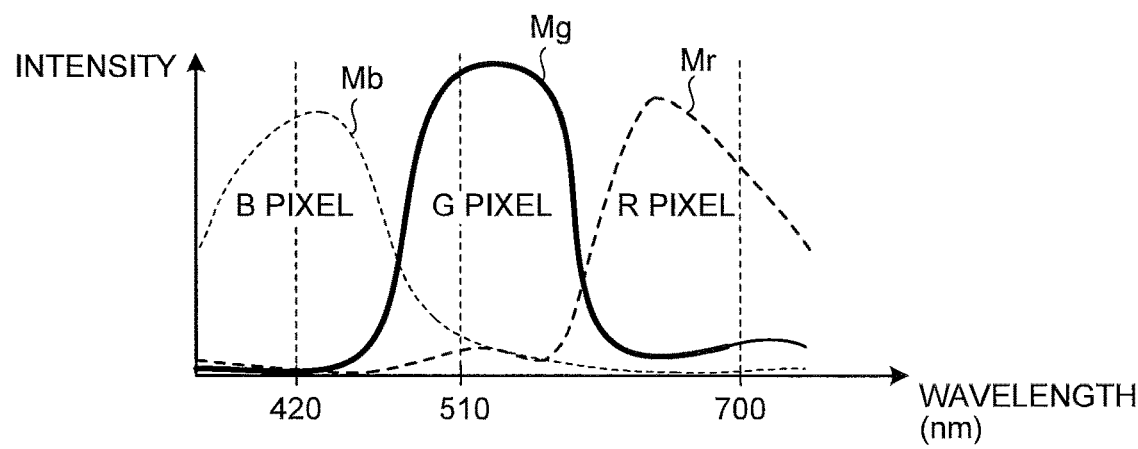
FIG. 3C is a diagram illustrating wavelength dependency of spectral sensitivity of an image sensor of an imaging unit, according to an embodiment.
Figure 4:
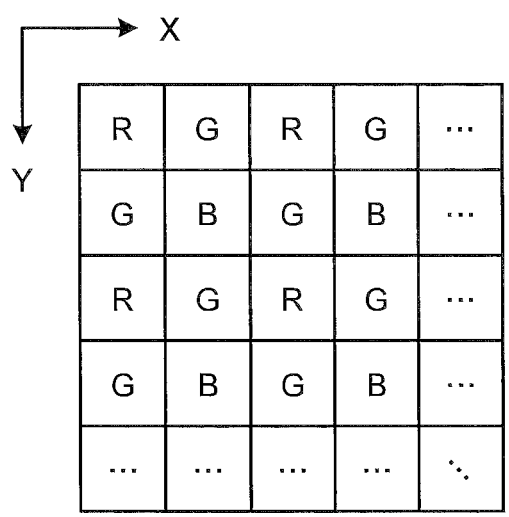
FIG. 4 is a diagram illustrating an exemplary pixel arrangement on an image sensor of an imaging unit illustrated in FIG. 2.

FIG. 3C is a diagram illustrating wavelength dependency of a spectral sensitivity of each of pixels of the image sensor of the imaging unit 24. As illustrated by a curved line $M_b$ in FIG. 3C, the B pixel has sensitivity to light having a wavelength 390 nm to 470 nm including blue light (hereinafter, B light) on the image sensor of the imaging unit 24. As illustrated by a curved line $M_g$ in FIG. 3C, the G pixel has sensitivity to green light (hereinafter, G light) having a wavelength of 470 nm to 580 nm. As illustrated by a curved line $M_r$ in FIG. 3C, the R pixel has sensitivity to light having a wavelength 650 nm to 800 nm, including red light (hereinafter, R light). FIG. 4 is a diagram illustrating an exemplary pixel arrangement on the image sensor of the imaging unit illustrated in FIG. 2. As illustrated in FIG. 4, on a light receiving plane of the image sensor of the imaging unit 24, R pixels, G pixels, and B pixels are arranged in the Bayer array. This array includes odd lines and even lines alternately arranged in a column direction (y-direction). The odd line includes the G pixels and the R pixels alternately arranged in a row direction (x-direction). The even line includes the B pixels and the G pixels alternately arranged in the row direction.

Figure 9:
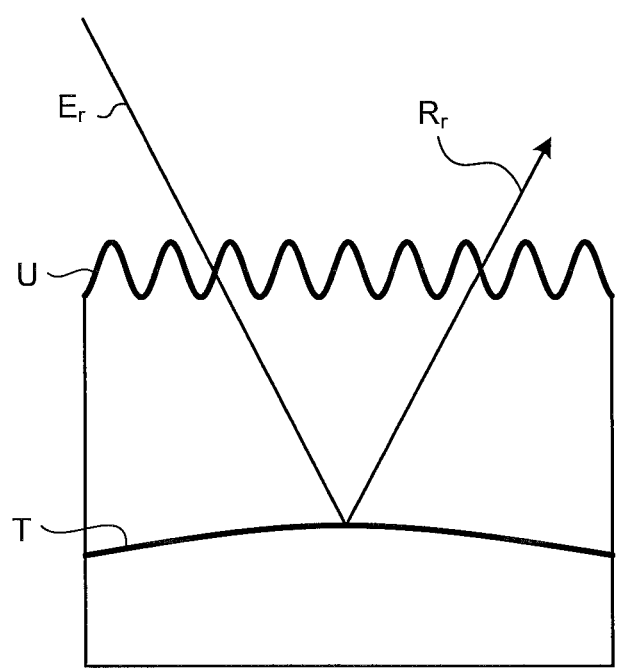
FIG. 9 is a schematic diagram illustrating return light from a biological tissue when irradiated with light for a fluorescence differential image.
Figure 10:
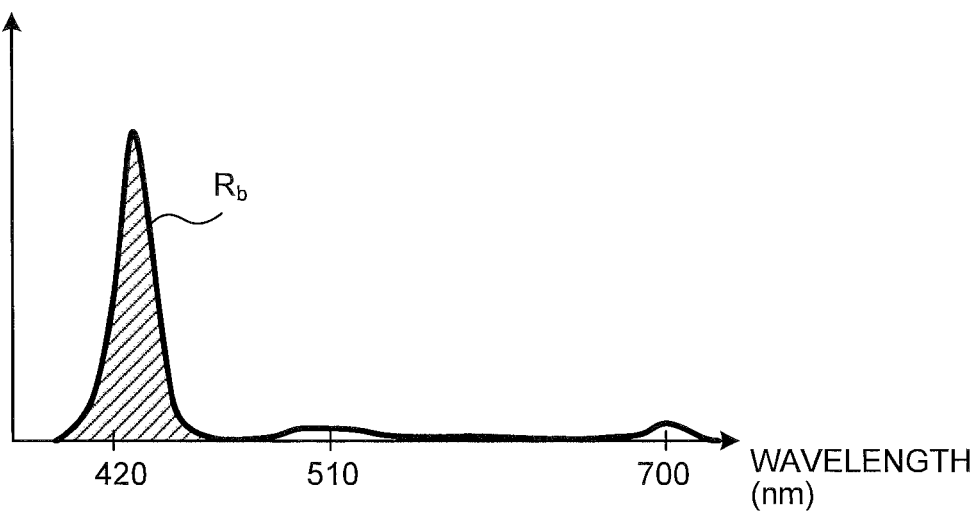
FIG. 10 is a diagram illustrating spectral characteristics of light reception data of a B pixel that has received light that returns from a biological tissue when irradiated with the light for a fluorescence differential image.
Figure 11:
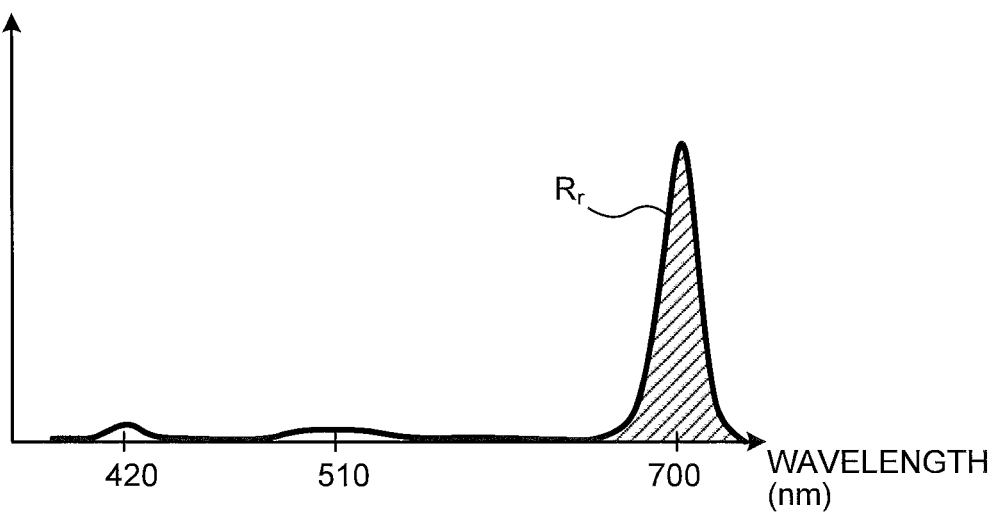
FIG. 11 is a diagram illustrating spectral characteristics of light reception data of R pixel that has received light that returns from a biological tissue when irradiated with the light for a fluorescence differential image.

Reference will be made to the return light from a biological tissue (mucosal tissue) when the biological tissue inside the subject is irradiated with the light for a fluorescence differential image. FIGS. 5, 6, 8, and 9 are schematic diagrams illustrating return light from a biological tissue when irradiated with light $E_b$ and $E_r$ for a fluorescence differential image. FIG. 7 is a diagram illustrating spectral characteristics of light reception data of a G pixel that has received light returning from a biological tissue when irradiated with the light $E_b$ and $E_r$ for a fluorescence differential image. FIG. 10 is a diagram illustrating spectral characteristics of light reception data of B pixel that has received light returning from a biological tissue when irradiated with the light $E_b$ and $E_r$ for a fluorescence differential image. FIG. 11 is a diagram illustrating spectral characteristics of light reception data of R pixel that has received light returning from a biological tissue when irradiated with the light $E_b$ and $E_r$ for a fluorescence differential image.

Figure 5:
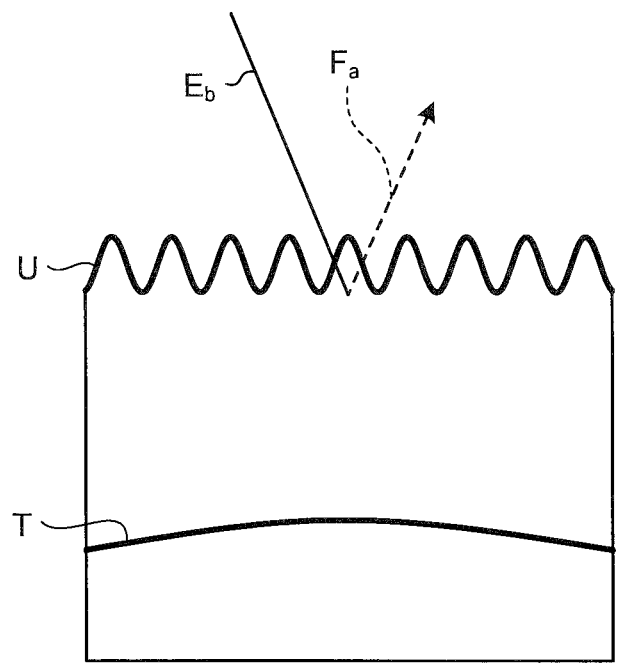
FIG. 5 is a schematic diagram illustrating return light from a biological tissue when irradiated with light for a fluorescence differential image.
Figure 6:
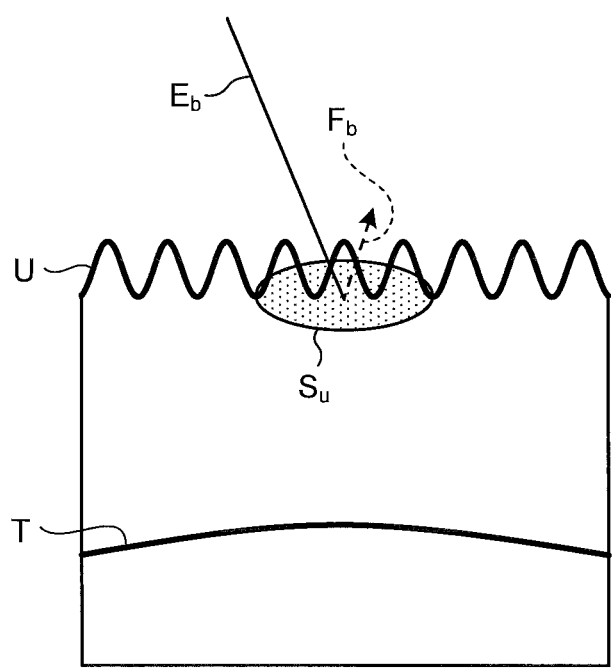
FIG. 6 is a schematic diagram illustrating return light from a biological tissue when irradiated with light for a fluorescence differential image.
Figure 7:
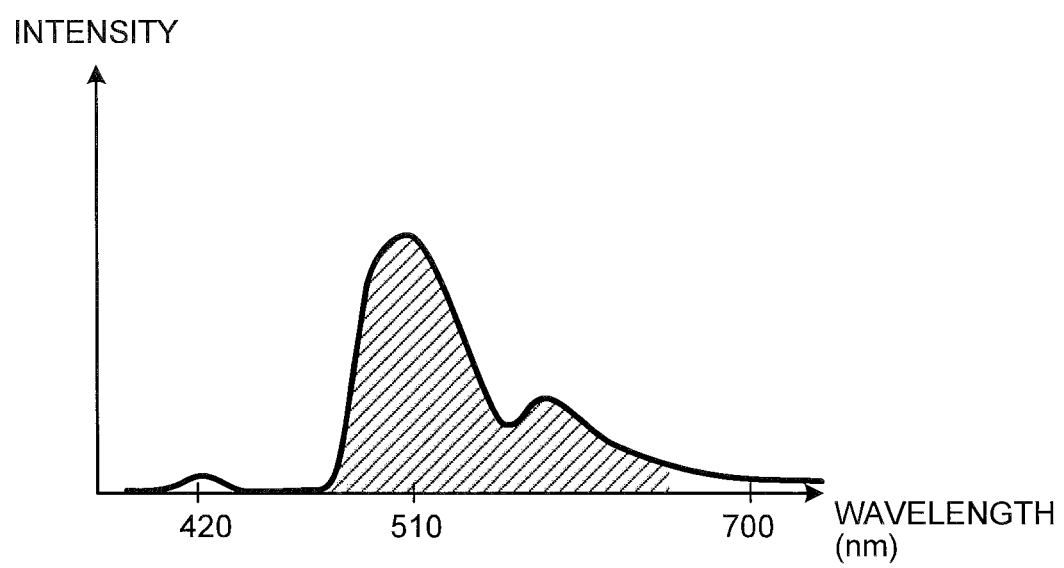
FIG. 7 is a diagram illustrating spectral characteristics of light reception data of G pixel that has received light that returns from a biological tissue when irradiated with the light for a fluorescence differential image.

As illustrated in FIGS. 5 and 6, when the light $E_b$, and $E_r$ for a fluorescence differential image is incident on a mucosal tissue of a living body, the mucosal tissue, excited by the light $E_b$, emits autofluorescence having a peak at wavelength 510 nm. As described above, the autofluorescence has a peak at a wavelength 510 nm, having intensity mainly in the wavelength 500 nm to 600 nm, and thus, the G pixel of the imaging unit 24 receives most of the autofluorescence (refer to FIG. 7). Accordingly, the G light received by the G pixel when the light $E_b$ and $E_r$ for a fluorescence differential image is emitted corresponds to autofluorescence from the biological tissue. Moreover, the intensity is lower in an autofluorescence $F_b$ (refer to FIGS. 6 and 3B) in an abnormal site $S_u$ (refer to FIG. 6) having mucosal abnormalities than in autofluorescence $F_a$ (refer to FIGS. 5 and 3B) in a normal site.

Figure 8:
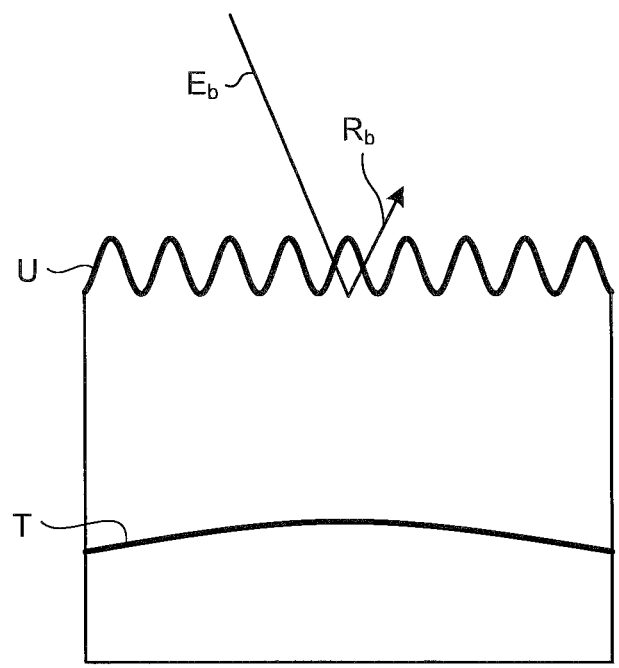
FIG. 8 is a schematic diagram illustrating return light from a biological tissue when irradiated with light for a fluorescence differential image.

As illustrated in FIG. 8, a portion of the light $E_b$ among the light for a fluorescence differential image has a short wavelength, and thus, is entirely reflected from a mucosal surface layer U and becomes reflected light $R_b$. As illustrated in FIG. 9, the light $E_r$ having a peak at a wavelength 700 nm among the light for a fluorescence differential image has a long wavelength. Therefore, when being incident on the mucosal tissue, the light $E_r$ enters an inner portion of the mucosal tissue, reflected at a deep portion T of the mucosal tissue, and becomes reflected light $R_r$. On the imaging unit 24, the B pixel receives reflected light $R_b$ (refer to FIG. 10), and the R pixel receives reflected light $R_r$ (refer to FIG. 11). The image signals generated by the B pixel and the R pixel that have received the reflected light $R_b$ and $R_r$ respectively when the light $E_b$ and $E_r$ for a fluorescence differential image is emitted include few signals corresponding to autofluorescence from the biological tissue.

Accordingly, the differential image generation unit 33c estimates an image signal of the G pixel that has received the reflected light of the G light including no autofluorescence using the image signals of the B and R pixels that have received the reflected light $R_b$ and $R_r$ including no autofluorescence, and then, generates a fluorescence differential image signal by employing the estimated image signal of the G light as a reference image signal.

On the differential image generation unit 33c, the extracting unit 33e firstly extracts from an image signal of one frame as a processing target, a first image signal generated by the B pixel that has actually received reflected light $R_b$ having a wavelength of 390 nm to 470 nm, as first wavelength band, and by the R pixel that has actually received reflected light $R_r$ having a wavelength 650 nm to 800 nm, as the light of the first wavelength band. The extracting unit 33e also extracts a second image signal generated by the G pixel that has actually received autofluorescence having a wavelength of 500 nm to 600 nm, namely, the light of the second wavelength band.

Based on the first image signal extracted by the extracting unit 33e, the estimation unit 33f performs calculation processing for estimating an image signal to be generated by the G pixel that has received autofluorescence having a wavelength of 500 nm to 600 nm in the second wavelength band.

The difference calculation unit 33g employs, as a reference image signal, the image signal that is estimated by the estimation unit 33f (estimated image signal) and is to be generated by the G pixel that has received autofluorescence having a wavelength of 500 nm to 600 nm. The difference calculation unit 33g calculates a difference, on a corresponding image portion, between the second image signal generated by the G pixel that has received autofluorescence having a wavelength of 500 nm to 600 nm extracted by the extracting unit 33e, and the estimated image signal estimated by the estimation unit 33f, and thereby generates a fluorescence differential image signal.

Figure 12:
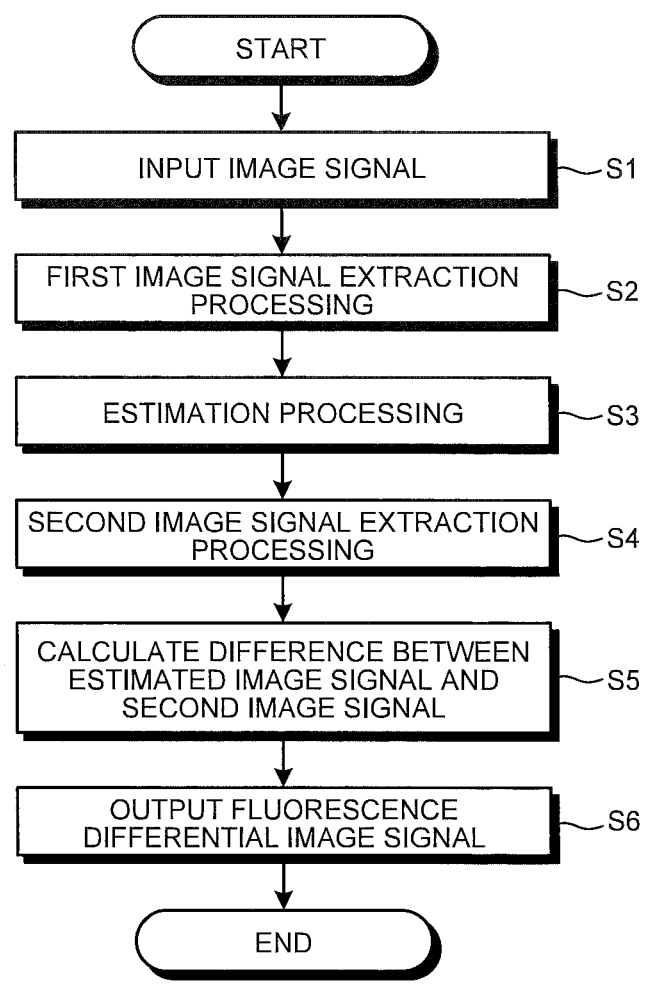
FIG. 12 is a flowchart illustrating a processing procedure of fluorescence differential image generation processing performed by a differential image generation unit illustrated in FIG. 2.

FIG. 12 is a flowchart illustrating a processing procedure of fluorescence differential image generation processing performed by the differential image generation unit 33c. As illustrated in FIG. 12, when the image signal for fluorescence differential image generation for one frame as a processing target is input from the signal processing unit 33a, into the differential image generation unit 33c (step S1), the extracting unit 33e performs first image signal extraction processing (step S2) in which the first image signal that is an image signal generated by the pixel that has received the light of the first wavelength band, from the image signal for fluorescence differential image generation for one frame as a processing target.

Based on the first image signal extracted by the first image signal extraction processing, the estimation unit 33f performs estimation processing (step S3) that estimates the image signal to be generated by the G pixel that has received the light of the second wavelength band.

Figure 13:
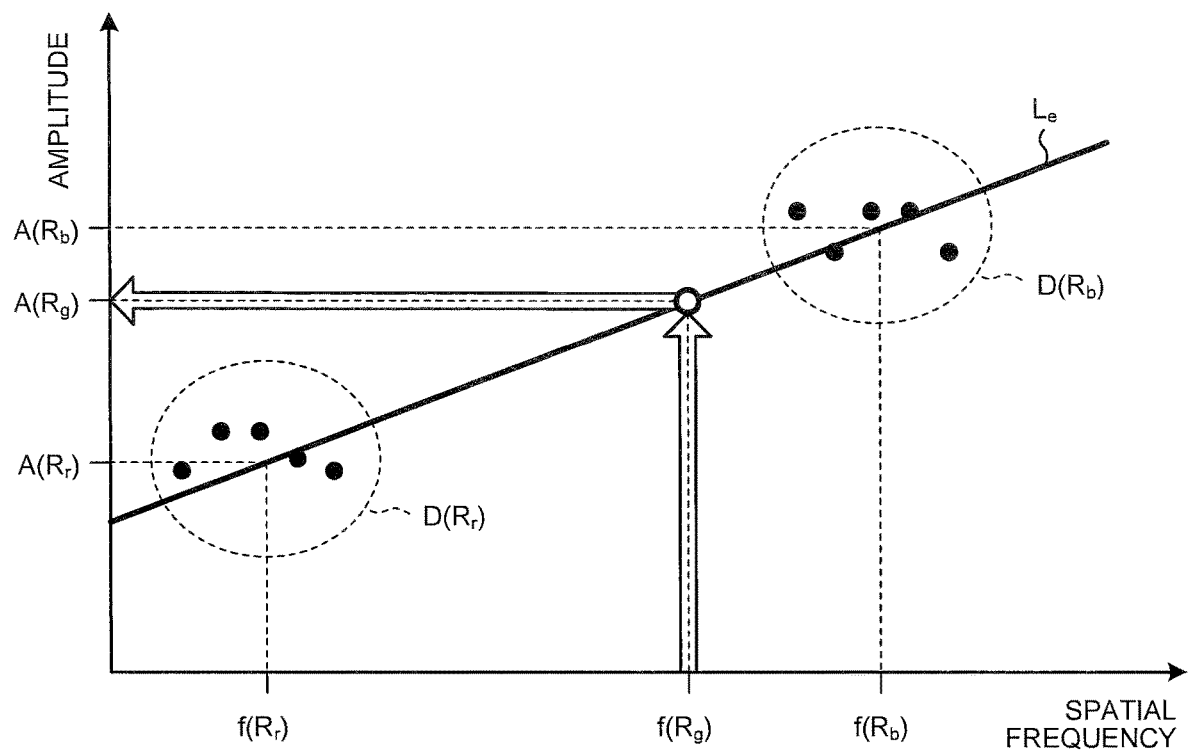
FIG. 13 is a diagram illustrating processing details of estimation processing illustrated in FIG. 12.

FIG. 13 is a diagram illustrating processing details of the estimation processing illustrated in FIG. 12. Note that FIG. 13 illustrates components of one axis alone. The estimation unit 33f performs second-dimensional discrete Fourier transform on the B pixel signal and the R pixel signal, as the first image signal, obtains an approximate expression from each of amplitude data. The estimation unit 33f, then, calculates amplitude at a middle spatial frequency (corresponding to a wavelength 510 nm) from the obtained approximate expression, and performs inverse Fourier transform to generate an image signal having a wavelength of 510 nm.

Specifically, based on the B image signal as the first image signal, an average spatial frequency $f(R_b)$ of the B pixel that has received the reflected light $R_b$ from the discrete Fourier transform data $D(R_b)$ of the B pixel that has received the reflected light $R_b$ having a peak wavelength 420 nm is obtained, and then, amplitude data $A(R_b)$ at $f(R_b)$ is calculated. Similarly, based on the R image signal as the first image signal, the estimation unit 33f obtains an average spatial frequency $f(R_r)$ of the R pixel that has received the reflected light $R_r$ from the discrete Fourier transform data $D(R_r)$ of the R pixel that has received the reflected light $R_r$ having a peak wavelength 700 nm, and then, obtains amplitude data $A(R_r)$ at $f(R_r)$. The estimation unit 33f obtains an approximate expression $L_e$ using linear approximation, based on the average spatial frequency $f(R_b)$ of the B pixel, the average spatial frequency $f(R_r)$ of the R pixel, the amplitude data $A(R_b)$ of the B pixel, and the amplitude data $A(R_r)$ of the R pixel. Although linear approximation is used as the approximate expression in FIG. 13, it is allowable to perform approximation using a higher order expression such as a cubic expression based on findings obtained beforehand by actual measurement, or the like.

Subsequently, based on the obtained approximate expression $L_e$, the estimation unit 33f calculates amplitude data $A(R_g)$ of the average spatial frequency $f(R_g)$ of the reflected light corresponding to a middle wavelength 510 nm between the wavelength 420 nm and the wavelength 700 nm. The estimation unit 33f performs inverse Fourier transform using the calculated amplitude data $A(R_g)$, and estimates the image signal to be generated on the G pixel that has received reflected light having a wavelength 510 nm. The image signal estimated by the estimation processing performed by the estimation unit 33f is an image signal of the G light generated based on the reflected light $R_b$ and the reflected light $R_r$ including no autofluorescence, namely, a G image signal obtained by receiving G light including no autofluorescence, and is employed as a reference image signal.

The extracting unit 33e performs second image signal extraction processing (step S4) that extracts a second image signal from the image signal for fluorescence differential image generation in a frame same as the frame of the image signal for which the first image signal has been extracted in step S2.

The difference calculation unit 33g calculates a difference (step S5), on a corresponding image portion, between the image signal (estimated image signal) estimated in the estimation processing (step S3), and the second image signal extracted in the second image signal extraction processing (step S4).

Figure 14:
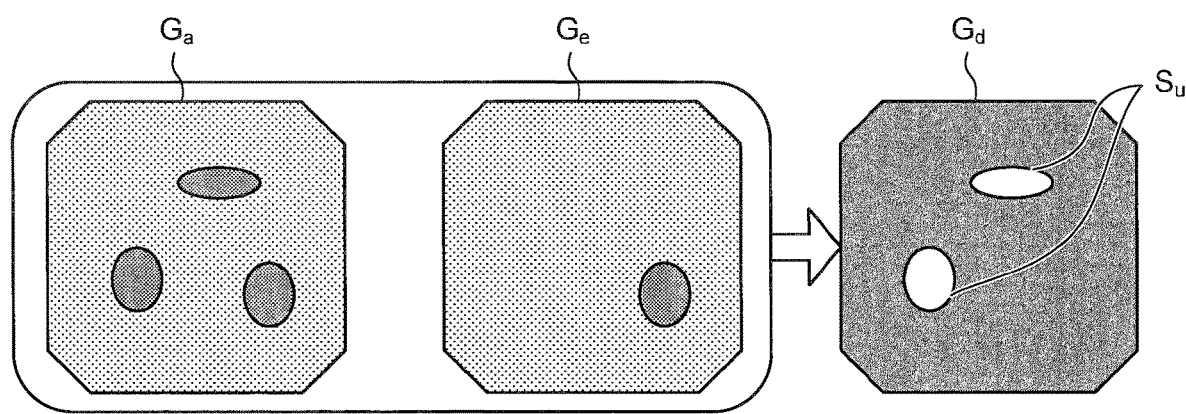
FIG. 14 is a schematic diagram illustrating difference calculation processing performed by a difference calculation unit illustrated in FIG. 12.

FIG. 14 is a schematic diagram illustrating difference calculation processing at the difference calculation unit 33g. An extracted image $G_a$ illustrated in FIG. 14 is an image corresponding to the extracted second image signal, namely, the image signal generated by the G pixel that has actually received autofluorescence. Meanwhile, the estimated image $G_e$ is an image corresponding to an image signal estimated by the estimation unit 33f, namely, the G image signal (reference image signal) that has received the G light including no autofluorescence. By calculating the difference, on a corresponding image, between the extracted image $G_a$ and the estimated image $G_e$, the difference calculation unit 33g can generate a fluorescence differential image $G_d$ in which noise is canceled and thus, an abnormal site $S_u$ is highlighted due to an amplified imaging signal for the abnormal site.

The differential image generation unit 33c outputs the fluorescence differential image signal generated by the difference calculation unit 33g to the abnormal image determination unit 33d (step S6) and finishes fluorescence differential image generation processing. The fluorescence differential image signal generated by the differential image generation unit 33c is determined whether the image is an abnormal image, by comparison of a differential value of each of image regions with a predetermined value, by the abnormal image determination unit 33d. The predetermined value is set, for example, based on an image signal of a G pixel that has received green autofluorescence emitted from an abnormal site and an image signal of a G pixel that has received a reflected light from a biological tissue in a case where G light having a wavelength band same as the wavelength band of fluorescence, having been obtained beforehand, is emitted. Subsequently, the fluorescence image signal output from the image processing unit 33 is first converted into a differential image display image signal in which an image portion having a differential value larger than a predetermined value is displayed in a color distinguishable from other portions, by the differential image display controller 34b, and thereafter, is output and displayed onto the display device 5. If the image is an abnormal image, the image signal is output and displayed onto the display device 5 while an abnormal flag is set.

In this manner, in the first embodiment, based on the first image signal generated by the B pixel and the R pixel that have received reflected light $R_b$ and $R_r$ from the biological tissue irradiated with illumination light, among the image signals as processing targets, the image signal to be generated by the G pixel that has received reflected light including no autofluorescence when G light is emitted, is estimated. Subsequently, by defining the estimated image signal as a reference image signal, a fluorescence differential image signal for one sheet is generated by calculating the difference between the estimated image signal and the second image signal generated by the G pixel that has actually received autofluorescence among the image signals as processing targets. In other words, in the first embodiment, an image signal including no autofluorescence is estimated based on an image signal obtained by one-time emission of light for a fluorescence differential image, and a portion having less autofluorescence is automatically detected as an image having an abnormal site portion based on a difference between the estimated image signal and the image signal including autofluorescence. With this configuration, according to the first embodiment, it is possible, with image signals of one frame, to generate a fluorescence differential image signal for one sheet. Therefore, it is possible to generate a fluorescence differential image signal highlighting an abnormal site, more efficiently than a known technique that requires image signals for two frames in order to generate a fluorescence differential image signal for one sheet.

In the first embodiment, an abnormal flag is set to a fluorescence differential image signal having an abnormal site, among generated fluorescence differential image signals, so as to easily distinguish an abnormal image signal from other image signals. This configuration makes it possible for an operator to promptly find an abnormal image signal from a large number of fluorescence differential image signals.

Also in the first embodiment, an abnormal site in the fluorescence differential image signal is displayed in a color distinguishable from other portions. This configuration makes it possible for the operator to easily identify the position of the abnormal site among the fluorescence differential image signal to which the abnormal flag has been set.

Although the first embodiment describes an exemplary case in which the estimation unit 33f obtains an estimated image signal using the image signal generated by the B pixel and the image signal generated by the R pixel, it is not limited to this example. In a case where there are findings obtained beforehand by actual measurement, or the like, it is possible to set the order of function to be used for approximation in the approximate expression $L_e$. Accordingly, in this case, the estimation unit 33f can estimate the image signal of the middle G pixel as long as there is any one of the image signals of the B pixel and the R pixel. In this case, it would be sufficient that the estimation unit 33f performs estimation processing based on any one of the image signals of the B pixel and the R pixel extracted from the image signals as processing targets, and on the settings regarding the preset approximate expression.

Moreover, in the first embodiment, the light $E_b$, among the light of the first wavelength band, would be merely required to excite a biological tissue. Therefore, the light is not limited to the wavelength range of 390 nm to 470 nm, but may be light with a wavelength band including a wavelength that can excite a biological tissue. The peak wavelength is not limited to 510 nm. Among the light of the first wavelength band, the light $E_r$ would not affect calculation processing at the estimation unit 33f as long as it is light that can be received by the R pixel. Accordingly, the light is not limited to the light having a wavelength of 650 nm to 800 nm, but may be visual light or near-infrared light.

Second Embodiment

Figure 15:
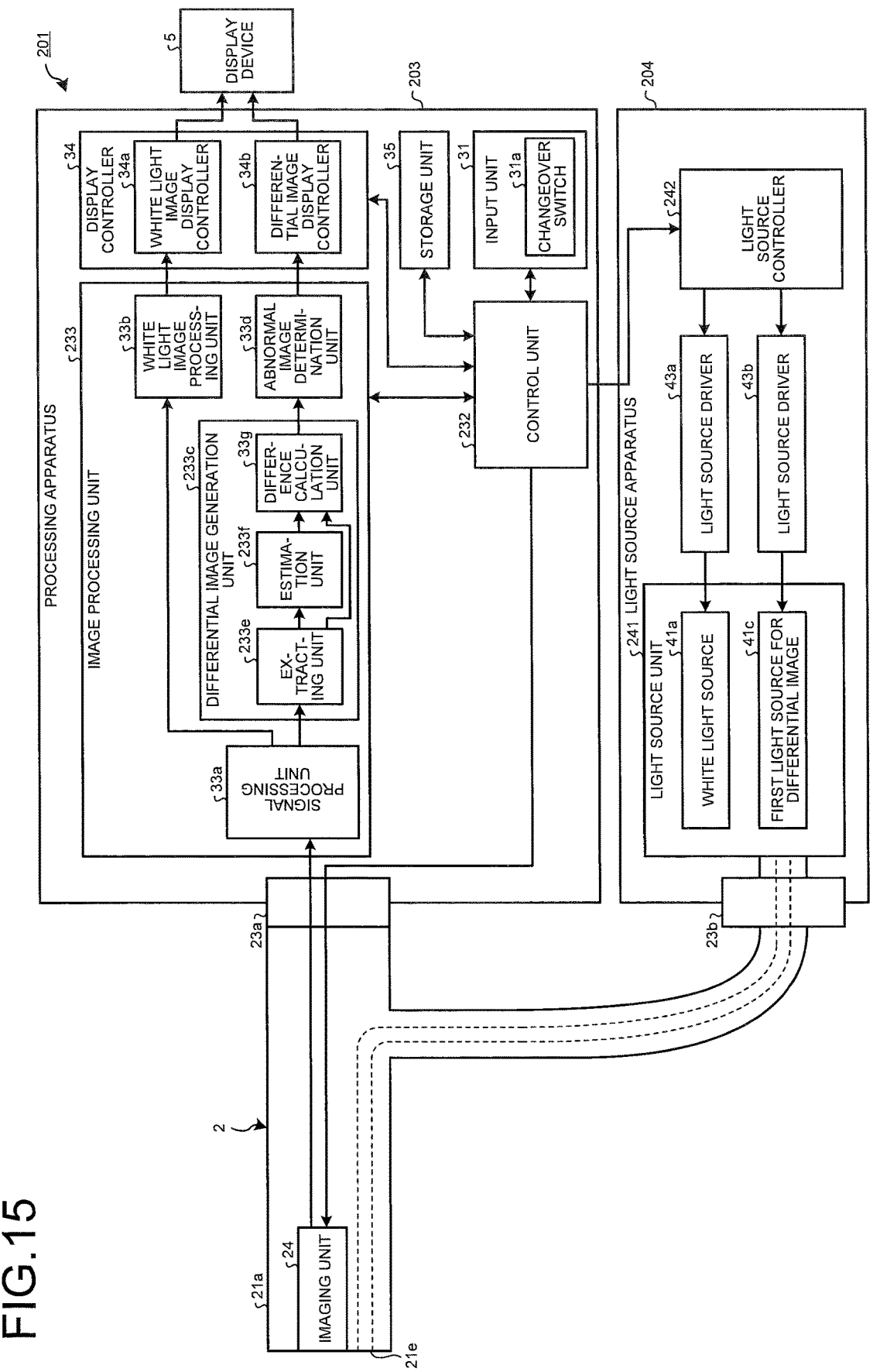
FIG. 15 is a block diagram schematically illustrating a configuration of an endoscope system according to a second embodiment.

Next, a second embodiment will be described. In the second embodiment, reference will be made to a case in which the fluorescence differential image signal is generated by solely emitting the light $E_b$, namely, fluorescence excitation light, as the light of the first wavelength band. FIG. 15 is a block diagram schematically illustrating a configuration of an endoscope system according to the second embodiment.

As illustrated in FIG. 15, an endoscope system 201 according to the second embodiment includes a processing apparatus 203 and a light source apparatus 204. The processing apparatus 203 includes an image processing unit 233. The image processing unit 233 includes a differential image generation unit 233c having an extracting unit 233e and an estimation unit 233f, respectively, in place of the extracting unit 33e and the estimation unit 33f. The processing apparatus 203 includes a control unit 232 having functions similar to the function of the control unit 32. The light source apparatus 204 includes a light source unit 241 and a light source controller 242. The light source unit 241 has no light source driver 43c and no second light source 41d for differential image.

Figure 16A:
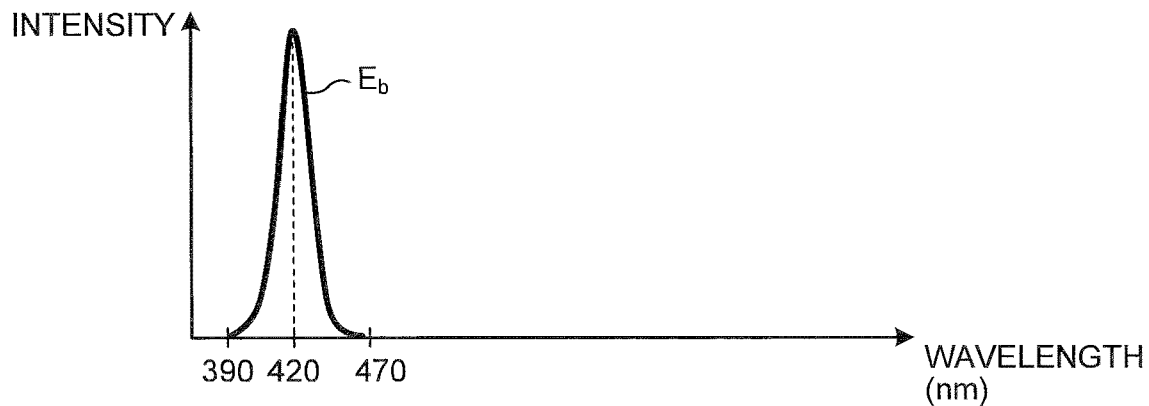
FIG. 16A is a diagram illustrating wavelength dependency of spectral characteristics of a light source for a differential image illustrated in FIG. 15.
Figure 16B:
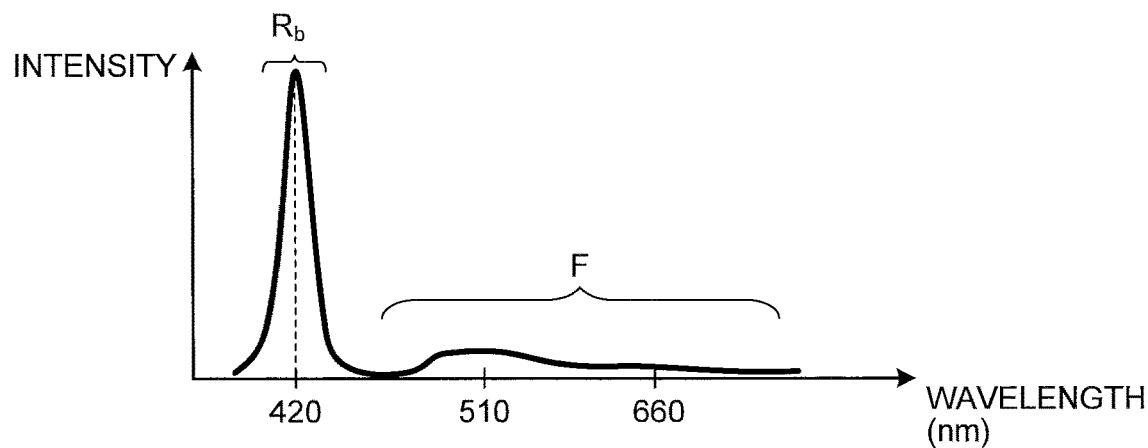
FIG. 16B is a diagram illustrating spectral characteristics of autofluorescence of a biological tissue.
Figure 16C:
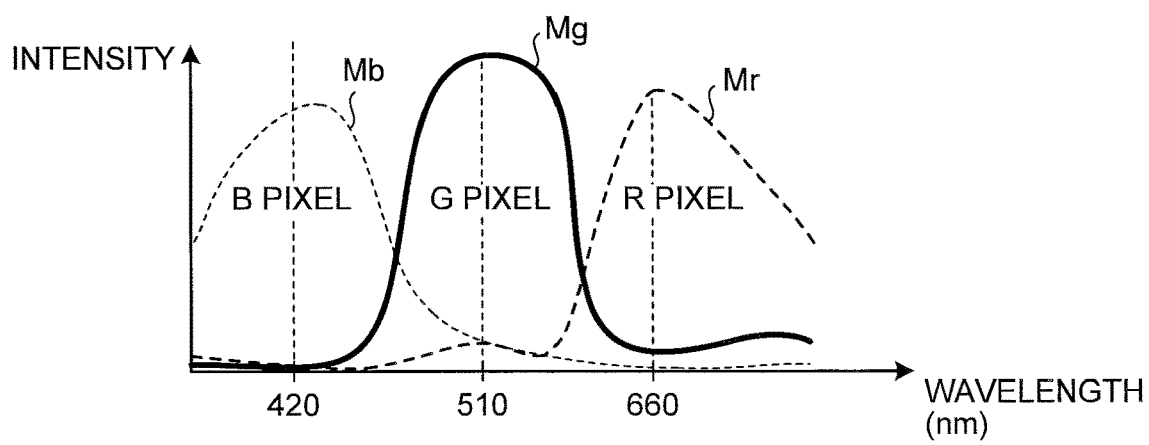
FIG. 16C is a diagram illustrating wavelength dependency of spectral sensitivity of an image sensor of an imaging unit illustrated in FIG. 15 and illustrating a light reception level of each of pixels.
Figure 17:
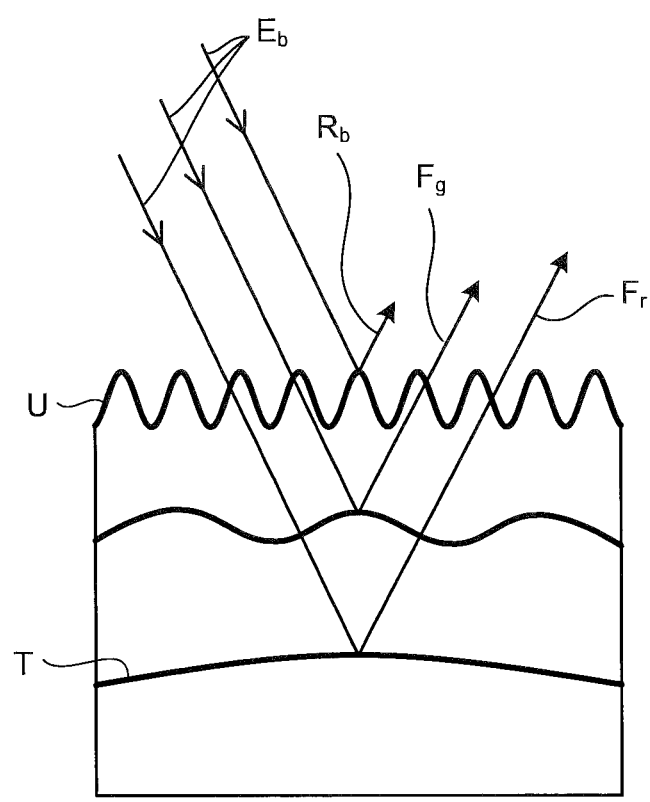
FIG. 17 is a schematic diagram illustrating return light from a biological tissue when irradiated with light for a fluorescence differential image, according to the second embodiment.

FIG. 16A is a diagram illustrating wavelength dependency of spectral characteristics of a light source for a differential image according to the second embodiment. FIG. 16B is a diagram illustrating spectral characteristics of return light from a biological tissue (mucosal tissue). FIG. 16C is a diagram illustrating wavelength dependency of a spectral sensitivity of each of pixels on an image sensor of the imaging unit 24 and illustrating a light reception level of each of the pixels. FIG. 17 is a schematic diagram illustrating return light from a biological tissue (mucosal tissue) when irradiated with light $E_b$ for a fluorescence differential image.

As illustrated in FIG. 16A, the light source apparatus 204 emits a fluorescence excitation light, specifically, the light $E_b$ alone, having a wavelength of 390 nm to 470 nm (peak wavelength: 420 nm) as the light of the first wavelength band, namely, the light for a fluorescence differential image. When the biological tissue is irradiated with the light $E_b$, a portion of the light $E_b$ is entirely reflected from a mucosal surface layer U (reflected light $R_b$ in FIG. 17), and the reflected light $R_b$ (refer to FIG. 16B) is received by the B pixel (refer to FIG. 16C) having sensitivity to the light having a wavelength of 390 nm to 470 nm. The image signal generated by the B pixel includes no signal that corresponds to the autofluorescence F from the biological tissue.

Most portion of the light $E_b$ is made incident on an internal portion of the mucosal tissue, excites the mucosal tissue, and causes the mucosal tissue to generate autofluorescence F (refer to FIG. 16B). Among the autofluorescence F, autofluorescence $F_g$ (refer to FIG. 17), in which intensity mainly exists, having a wavelength of 500 nm to 600 nm (peak wavelength: wavelength 510 nm as the first peak wavelength) is received by the G pixel (refer to FIG. 16C).

A portion of the light $E_b$ comes into a deep portion T of the mucosal tissue, excites the mucosal tissue of the deep portion T, and causes the mucosal tissue to generate autofluorescence F. Among the autofluorescence F generated in the deep portion T of the mucosa, autofluorescence $F_g$ having a short wavelength of 500 nm to 600 nm attenuates before it reaches the mucosal surface layer U. Accordingly, the autofluorescence emitted from the deep portion T to the outside is mainly autofluorescence $F_r$ (refer to FIG. 17) having a long wavelength of 650 nm to 800 nm (peak wavelength: 660 nm as second peak wavelength). The autofluorescence $F_r$ is received by the R pixel (refer to FIG. 16C).

When the biological tissue is a mucosal tissue, the structure is more complicated in a surface layer than in a deep portion, and thus, autofluorescence frequency is higher. Incidentally, an abnormal mucosa tends to exist in the vicinity of the surface layer to middle layers. Among the autofluorescence F, the autofluorescence $F_r$ is generated by excitation of the light $E_b$ that is transmitted through the mucosal surface layer U having a complicated structure and has reached the deep portion T of the mucosa. The structure of the deep portion T of the mucosa is merely influenced by the shape of the gastrointestinal tract, and thus, has fixed uniformity, with less irregularities than the mucosal surface layer U Therefore, it is possible to assume that the autofluorescence $F_r$ from the deep portion T is not influenced by the abnormal mucosa in the vicinity of the mucosal surface layer U, and thus, to assume that the autofluorescence $F_r$ includes no autofluorescence from the abnormal site in the mucosal surface layer U. Therefore, the image signal generated by the R pixel can be considered as a signal based on a mucosal tissue having fixed normality and is a signal unrelated to abnormal sites.

Accordingly, the differential image generation unit 233c estimates an image signal of the G pixel that has received the G light including no influence from autofluorescence in abnormal sites based on the image signals generated by the B pixels and R pixels that have been extracted from the image signals as processing targets, and employs the estimated image signal of the G light as a reference image signal.

Figure 18:
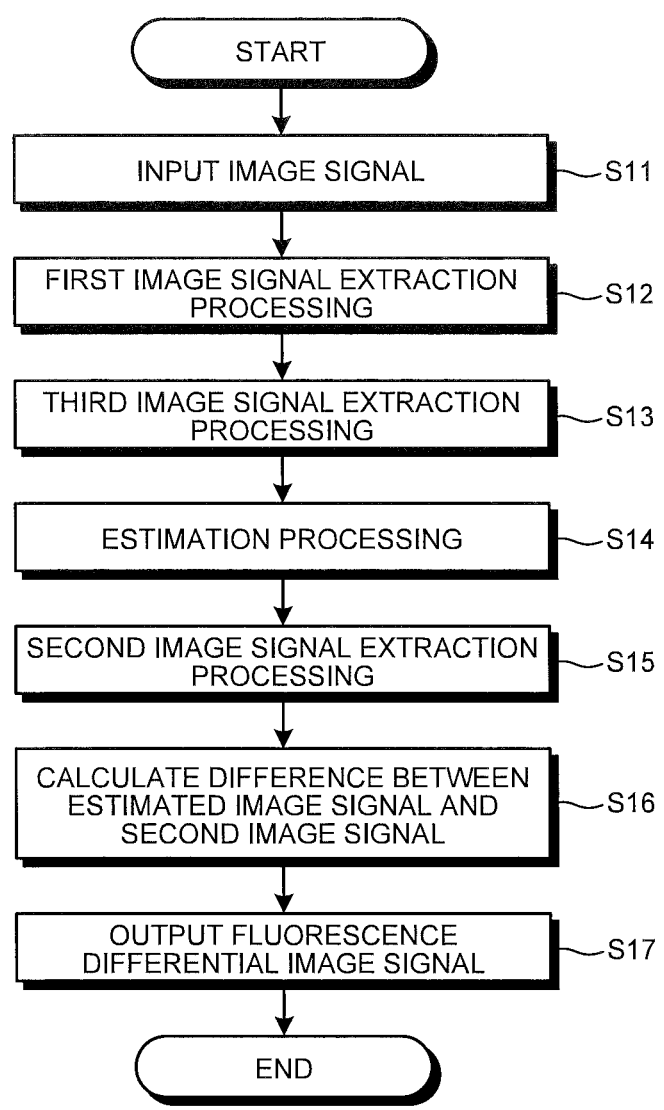
FIG. 18 is a flowchart illustrating a processing procedure of fluorescence differential image generation processing performed by a differential image generation unit illustrated in FIG. 15.

FIG. 18 is a flowchart illustrating a processing procedure of fluorescence differential image generation processing performed by the differential image generation unit 233c. Step S11 illustrated in FIG. 18 corresponds to step S1 illustrated in FIG. 12. The extracting unit 233e performs first image signal extraction processing (step S12) that extracts a first image signal from the image signal for fluorescence differential image generation for one frame, as processing target. In the second embodiment, the first image signal is an image signal generated by the pixel that has received reflected light of the light $E_b$ for a fluorescence differential image being the light of the first wavelength band, namely, the image signal generated by the B pixel that has received reflected light $R_b$ when the light $E_b$ is emitted.

The extracting unit 233e performs third image signal extraction processing (step S13) that extracts a third image signal from the image signal for fluorescence differential image generation in a frame same as the frame of the image signal for which the first image signal has been extracted in step S12. The third image signal is an image signal generated by the R pixel that has received light having a wavelength of 650 nm to 800 nm, namely, the autofluorescence $F_r$.

Based on the first image signal and the third image signal extracted by the extracting unit 233e, the estimation unit 233f performs estimation processing (step S14) that estimates the image signal to be generated by the G pixel that has received the light having a wavelength of 500 nm to 600 nm, namely, the second wavelength band.

Figure 19:
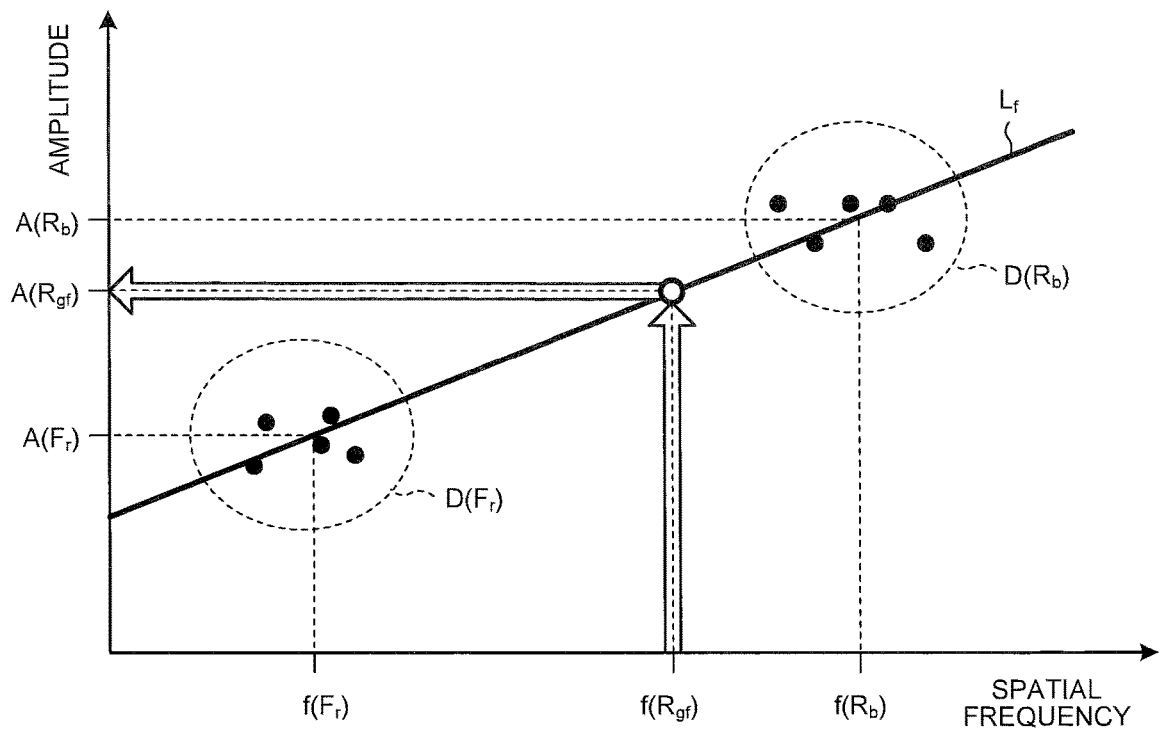
FIG. 19 is a diagram illustrating processing details of estimation processing illustrated in FIG. 18.

FIG. 19 is a diagram illustrating processing details of the estimation processing illustrated in FIG. 18. Note that FIG. 19 illustrates components of one axis alone. Similarly to the first embodiment, the estimation unit 233f obtains an average spatial frequency f ($R_b$) of the B pixel from the discrete Fourier transform data D ($R_b$) of the image signal of the B pixel, being the first image signal, and then, calculates amplitude data A ($R_b$) at f ($R_b$). The estimation unit 233f obtains the average spatial frequency f ($F_r$) of the R pixel from the discrete Fourier transform data D ($F_r$) of the image signal of the R pixel that has received red autofluorescence $F_r$, being the third image signal, and then, obtains amplitude data A ($F_r$) at f ($F_r$). Based on the average spatial frequency f ($R_b$) of the B pixel, the average spatial frequency f ($F_r$) of the R pixel, the amplitude data A ($R_b$), and the amplitude data A ($F_r$), the estimation unit 233f obtains an approximate expression $L_f$ using linear approximation. The approximate expression may be obtained by performing approximation using a higher order expression such as a cubic expression based on findings obtained beforehand by actual measurement, or the like.

Subsequently, based on the approximate expression $L_f$, the estimation unit 233f calculates amplitude data A ($R_{gf}$) of the average spatial frequency f ($R_{gf}$) that corresponds to the middle wavelength 510 nm between the wavelength 420 nm and the wavelength 660 nm. The estimation unit 233f performs inverse Fourier transform using the calculated amplitude data A ($R_{gf}$), and estimates the image signal to be generated by the G pixel that has received reflected light having the wavelength 510 nm. The estimated image signal estimated by the estimation processing performed by the estimation unit 233f is an image signal of the G light generated based on the autofluorescence $F_r$ and the reflected light $R_b$ including no influence from abnormal sites, and is employed as a reference image signal.

Similarly to step S4 illustrated in FIG. 12, the extracting unit 233e performs extraction processing of the second image signal (step S15) that extracts a second image signal from the image signals as processing targets. The second image signal is the image signal generated by the G pixel that has received autofluorescence having a wavelength of 500 nm to 600 nm.

Similarly to step S5 illustrated in FIG. 12, the difference calculation unit 33g calculates a difference (step S16), on a corresponding image portion, between the image signal estimated in the estimation processing (step S14), and the second image signal extracted in the second image signal extraction processing (step S15).

Figure 20:
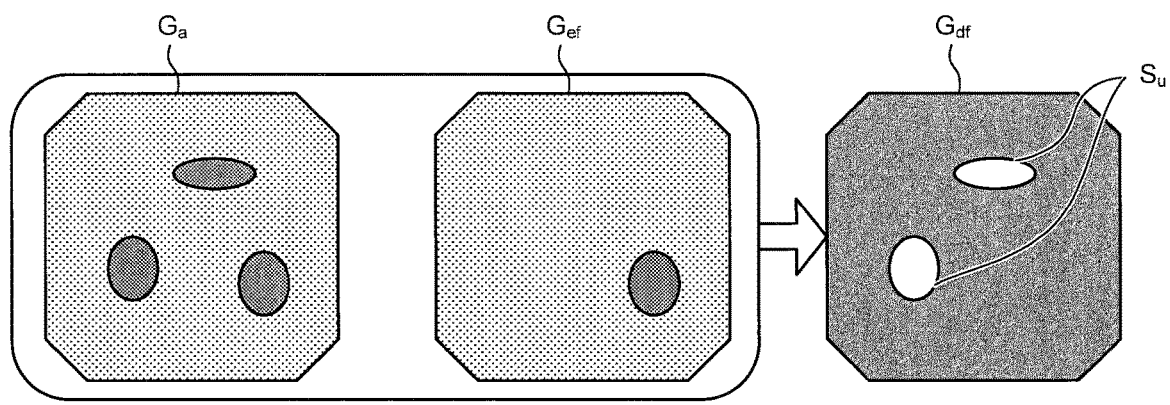
FIG. 20 is a schematic diagram illustrating difference calculation processing performed by a difference calculation unit illustrated in FIG. 18.

FIG. 20 is a schematic diagram illustrating difference calculation processing performed by the difference calculation unit 33g. As illustrated in FIG. 20, the difference calculation unit 33g generates a fluorescence differential image $G_{df}$ in which an abnormal site $S_u$ is highlighted, by calculating the difference, on a corresponding image portion, between the extracted image $G_a$ and the estimated image $G_{ef}$.

The differential image generation unit 233c outputs the fluorescence differential image signal generated by the difference calculation unit 33g to the abnormal image determination unit 33d (step S17), and finishes fluorescence differential image generation processing.

In the second embodiment, based on the pixel signal of B pixel that has received reflected light $R_b$ from the biological tissue irradiated with illumination light and on the pixel signal of the R pixel that has received the autofluorescence $F_r$ from the deep portion of the biological tissue, having little influence from an abnormal site, an image signal to be generated by the G pixel that has received reflected light including no autofluorescence when G light is emitted, is estimated. Subsequently, by employing the estimated image signal as a reference image signal, a fluorescence differential image signal for one sheet is generated from the image signal of one frame. Accordingly, with the second embodiment, it is possible to achieve an effect similar to the first embodiment. In addition, it would be sufficient to use merely the first light source 41c for differential image that emits light having a wavelength of 390 nm to 470 nm as fluorescence excitation light, as the light source needed for fluorescence differential image generation. As a result, it is possible to simplify the configuration compared with the first embodiment.

Although the second embodiment describes an exemplary case in which the estimation unit 233f obtains an estimated image signal using the image signal generated by the B pixel and the image signal generated by the R pixel, it is not limited to this example. In a case where there are findings obtained beforehand by actual measurement, or the like, it is possible to set the order of function to be used for approximation in the approximate expression $L_f$. Accordingly, in this case, the estimation unit 233f can estimate the image signal of the middle G pixel as long as there is any one of the image signals of the B pixel and the R pixel. In this case, it is possible omit step S12 or S13 in FIG. 18, and it would be sufficient in step S14 in FIG. 18 that the estimation unit 233f performs estimation processing based on any one of the image signals of the B pixel and the R pixel extracted from the image signals as processing targets, and on the settings for the preset approximate expression.

Moreover, in the second embodiment, the light $E_b$, being the light of the first wavelength band, would be merely required to excite a biological tissue. Therefore, the light is not limited to the wavelength range of 390 nm to 470 nm, but may be light with a wavelength band including a wavelength that can excite the biological tissue. The peak wavelength is not limited to 510 nm.

Third Embodiment

Next, a third embodiment will be described. In the third embodiment, reference will be made to an example in which the first embodiment is applied to a capsule endoscope system.

Figure 21:
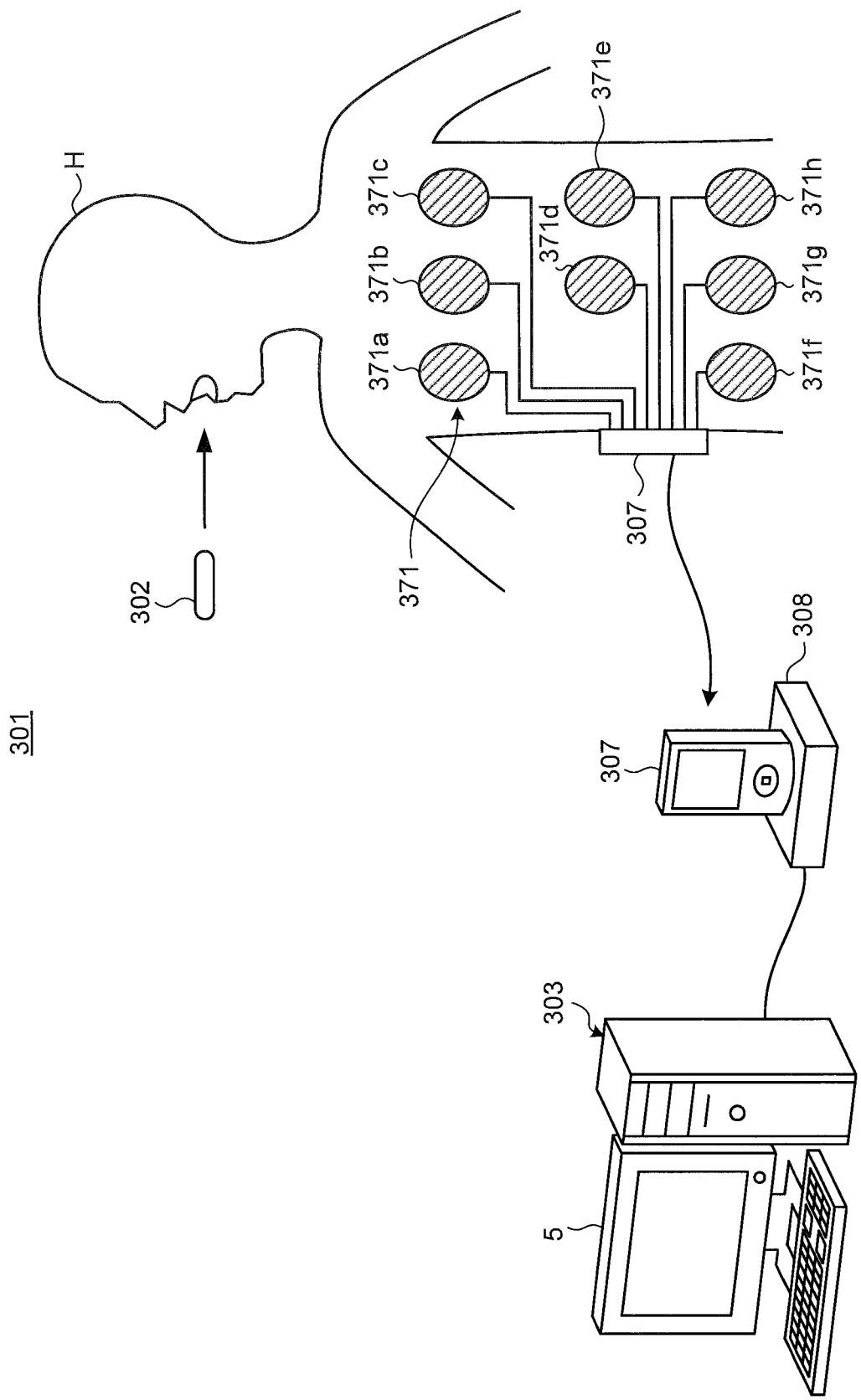
FIG. 21 is a schematic diagram illustrating a general configuration of a capsule endoscope system according to a third embodiment.

FIG. 21 is a schematic diagram illustrating a general configuration of a capsule endoscope system according to the third embodiment. As illustrated in FIG. 21, a capsule endoscope system 301 according to the third embodiment includes a capsule endoscope 302, a receiving device 307, and a processing apparatus 303. The capsule endoscope 302 is introduced into a subject H, images an internal portion of the subject H so as to obtain image data, and transmits the image data by superposing them over radio waves. The receiving device 307 receives radio signals transmitted from the capsule endoscope 302 via a receiving antenna unit 371 including a plurality of receiving antennas 371a to 371h attached to the subject H. The processing apparatus 303 fetches the image data obtained by the capsule endoscope 302 from the receiving device 307 via a cradle 308, and generates an image of the internal portion of the subject H using the image data. The image of the internal portion of the subject H, generated by the processing apparatus 303, is output and displayed, for example, onto the display device 5 connected to the processing apparatus 303.

Figure 22:
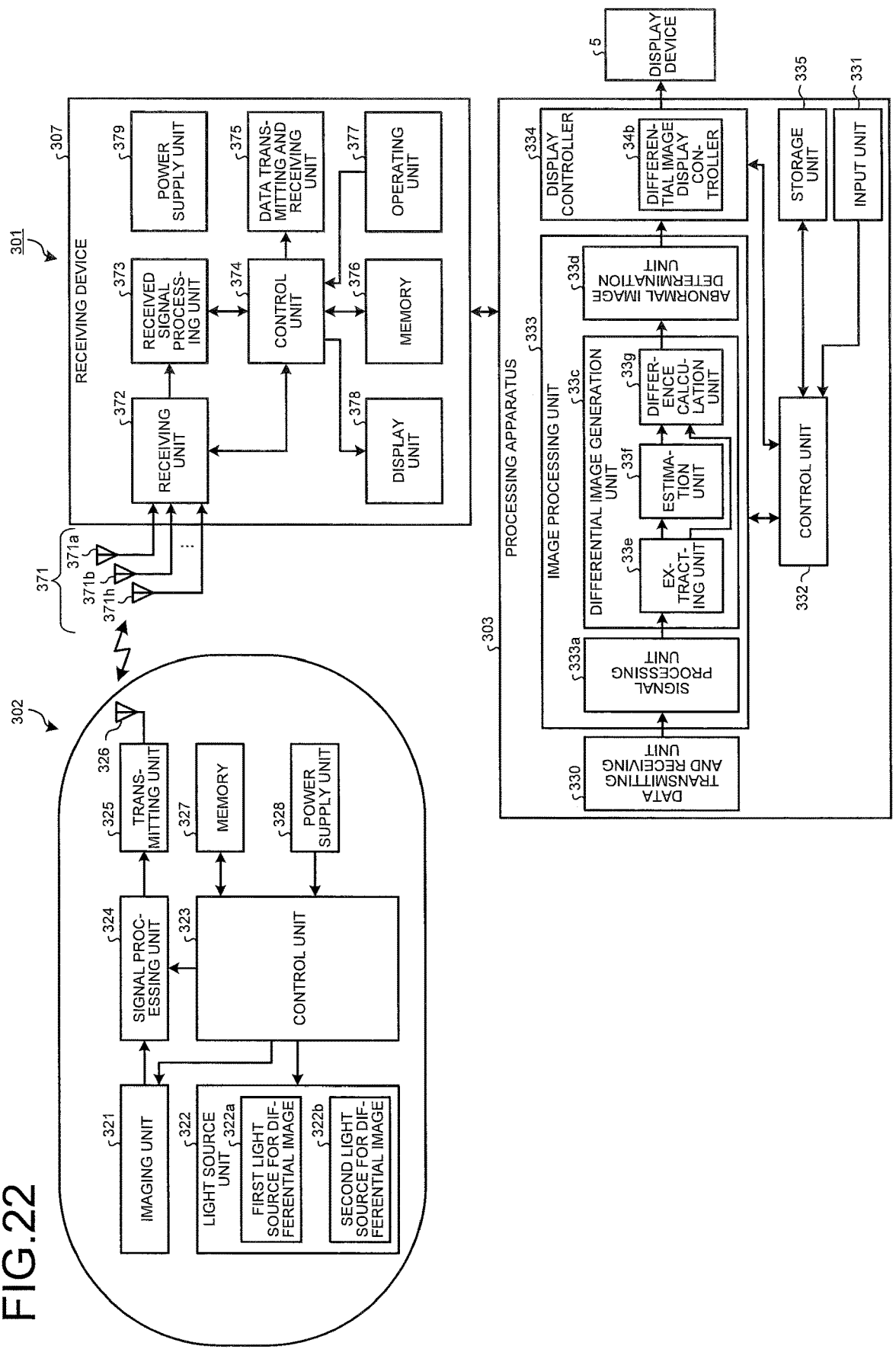
FIG. 22 is a block diagram illustrating configurations of a capsule endoscope apparatus, a receiving device, and a processing apparatus, illustrated in FIG. 21.

FIG. 22 is a block diagram illustrating configurations of the capsule endoscope 302, the receiving device 307, and the processing apparatus 303. The capsule endoscope 302 is an apparatus that incorporates various components such as an image sensor, in a casing having a capsule shape and a size that can be swallowed by the subject H. The capsule endoscope 302 includes an imaging unit 321, a light source unit 322, a control unit 323, a signal processing unit 324, a transmitting unit 325, an antenna 326, a memory 327, and a power supply unit 328. The transmitting unit 325 and the antenna 326 constitute a transmitter. The imaging unit 321 images an internal portion of the subject H. The light source unit 322 illuminates the internal portion of the subject H.

The imaging unit 321 includes an image sensor and an optical system. Exemplary image sensors include a CCD image sensor and a CMOS image sensor that generate an imaging signal representing an internal portion of the subject H from an optical image formed on a light receiving plane and output the imaging signal. The optical system includes an objective lens arranged on a light receiving plane side of the image sensor. The image sensor has a pixel arrangement similar to the image sensor on the imaging unit 24 in the first embodiment, in which a plurality of R, G, and B pixels that receives light from the subject H is arranged in a matrix, and each of the pixels photoelectrically converts the received light, thereby generating an image signal.

As the light for a fluorescence differential image (light of the first wavelength band), the light source unit 322 emits the light $E_b$, namely, the fluorescence excitation light, and the light $E_r$, similarly to the light source 41*b* for differential image in the first embodiment. The light source unit 322 includes a first light source 322*a* for a differential image and a second light source 322*b* for a differential image. The first light source 322*a* for a differential image includes an LED that emits light $E_b$ having a wavelength of 390 nm to 470 nm, namely, fluorescence excitation light. The second light source 41*d* for differential image includes an LED that emits light $E_r$ having a wavelength of 650 nm to 800 nm. When the biological tissue inside the subject H as an object is irradiated with the light $E_b$ having a wavelength of 390 nm to 470 nm, as described in the first embodiment, the B pixel of the imaging unit 321 receives the reflected light $R_b$ of the light $E_b$, and the R pixel receives the reflected light $R_r$ of the light $E_r$.

The control unit 323 controls operation processing on each of components of the capsule endoscope 302. The signal processing unit 324 processes an imaging signal output from the imaging unit 321. The signal processing unit 324 performs A/D conversion and predetermined signal processing on the imaging signal output from the imaging unit 321 and obtains digital-format imaging signal.

The transmitting unit 325 transmits the imaging signal output from the signal processing unit 324 to the outside from the antenna 326 with related information by superposing the signal over radio signals. The related information includes identification information (e.g., serial number) allocated for identification of the capsule endoscope 302.

The memory 327 stores a running program and a control program used by the control unit 323 to execute various operation. The memory 327 may temporarily store an imaging signal, or the like, that has undergone signal processing on the signal processing unit 324.

The power supply unit 328 includes a battery, a power supply circuit, and a power switch. The battery is a button battery, or the like. The power supply circuit performs step up, or the like, on the power from the battery. The power switch switches between on and off of the power supply unit 328. The power supply unit 328 supplies power to individual sections inside the capsule endoscope 302 after the power switch is turned on. The power switch is formed with, for example, a reed switch that is switched between on and off by an external magnetic force, and is switched to an on-state by applying an external magnetic force to the capsule endoscope 302 before use of the capsule endoscope 302 (before it is swallowed by the subject H).

The capsule endoscope 302 is swallowed by the subject H, and thereafter, moved inside the gastrointestinal tract of the subject H, with peristaltic action, or the like, of the organs and along with this movement, sequentially images biological sites (such as esophagus, stomach, small intestine, and large intestine) at a predetermined period (e.g. every 0.5 seconds). The image data obtained by the imaging operation and related information are sequentially transmitted to the receiving device 307 wirelessly.

The receiving device 307 includes a receiving a receiving unit 372, a received signal processing unit 373, a control unit 374, a data transmitting and receiving unit 375, a memory 376, an operating unit 377, a display unit 378, and a power supply unit 379 to supply power to these individual sections.

The receiving unit 372 receives the imaging signal wirelessly transmitted from the capsule endoscope 302 and related information via the receiving antenna unit 371 including a plurality of (eight in FIG. 21) receiving antennas 371*a* to 371*h*. Each of the receiving antennas 371*a* to 371*h* includes, for example, a loop antenna or a dipole antenna and to be arranged on a predetermined position on an external surface of the subject H.

The received signal processing unit 373 performs predetermined signal processing on the imaging signal received by the receiving unit 372. The control unit 374 controls individual components of the receiving device 307. The data transmitting and receiving unit 375 is an interface connectable to a USB, or a communication line such as wired LAN and wireless LAN. When the data transmitting and receiving unit 375 is connected to the processing apparatus 303 in a communicative state, the data transmitting and receiving unit 375 transmits the imaging signal and related information stored in the memory 376 to the processing apparatus 303.

The memory 376 stores the imaging signal that has undergone signal processing on the received signal processing unit 373 and its related information. The operating unit 377 is an input device used by a user when the user inputs various setting information and instruction information into the receiving device 307. The display unit 378 displays an in-vivo image, or the like, based on the image data received from the capsule endoscope 302.

The receiving device 307 is attached to and carried by the subject H during execution of imaging by the capsule endoscope 302 (for example, during the period after the capsule endoscope 302 is swallowed by the subject H until it is discharged after passing inside the gastrointestinal tract). During this period, the receiving device 307 further adds related information such as reception intensity information and reception time information on each of the receiving antennas 371*a* to 371*h*, to the imaging signal received via the receiving antenna unit 371, and stores these imaging signal and the related information into the memory 376.

After imaging by the capsule endoscope 302, the receiving device 307 is removed from the subject H and set to the cradle 308 connected to the processing apparatus 303 (refer to FIG. 21). With this arrangement, the receiving device 307 is connected with the processing apparatus 303 in a communicative state and transfers (downloads) the imaging signal and the related information stored in the memory 376 to the processing apparatus 303.

The processing apparatus 303 includes, for example, a workstation with a display device 5 such as a CRT display and a liquid crystal display. The processing apparatus 303 includes a data transmitting and receiving unit 330, an input unit 331, a control unit 332 that integrally controls individual sections of the processing apparatus 303, an image processing unit 333, a display controller 334, and a storage unit 335.

The data transmitting and receiving unit 330 is an interface connectable to a USB, or a communication lines such as wired LAN and wireless LAN and includes a USB and a LAN port. In the third embodiment, the data transmitting and receiving unit 330 is connected to the receiving device 307 via the cradle 308 connected to the USB port, and performs data transmission and reception with the receiving device 307.

The input unit 331 includes an input device such as a keyboard, mouse, touch-panel, and various switches. The input unit 331 receives input of information and commands in response to user's operation.

The control unit 332 includes hardware such as a CPU. The control unit 332 integrally controls overall operation of the processing apparatus 303, specifically, reads various programs stored by the storage unit 335 and thereby transmitting instruction and performing data transfer to individual sections of the processing apparatus 303 based on a signal input via the input unit 331 and on an imaging signal input from the data transmitting and receiving unit 330.

Under the control of the control unit 332, the image processing unit 333 performs predetermined image processing on the image signal input from the data transmitting and receiving unit 330 and on the image signal stored in the storage unit 335. The image processing unit 333 includes a signal processing unit 333a, the differential image generation unit 33c, and the abnormal image determination unit 33d. The signal processing unit 333a performs signal processing including optical black subtraction processing, gain adjustment processing, synchronization processing of an image signal, and gamma correction processing. The differential image generation unit 33c includes the extracting unit 33e, the estimation unit 33f, and the difference calculation unit 33g. The image signal as a processing target input from the data transmitting and receiving unit 330 is an image signal captured by the imaging unit 321 of the capsule endoscope 302. The image signal of one frame includes the image signal (second image signal) generated by the G pixel that has received autofluorescence having a wavelength of 500 nm to 600 nm (peak wavelength: 510 nm) in response to the light $E_b$, the image signals (first image signal) generated by the B pixel that has received the reflected light $R_b$ of the light $E_b$ and generated by the R pixel that has received the reflected light $R_r$ of the light $E_r$. Accordingly, the differential image generation unit 33c generates a fluorescence differential image signal by performing processing similar to the processing of generating a fluorescence differential image (refer to FIG. 12) executed by the differential image generation unit 33c in the first embodiment.

Similarly to the display controller illustrated in FIG. 2, the display controller 334 generates a display image signal to be displayed on the display device 5 from the image signal processed by the image processing unit 333. The display controller 334 includes the differential image display controller 34b.

Since the capsule endoscope is moved by peristaltic action of the gastrointestinal tract, there is a great level of imaging region variation between the frames. Therefore, an imaging region shift occurs between the image signals even in continuous frames. In this situation, it is difficult, with the capsule endoscope system, to use a known technique that requires image signals for two frames in order to generate fluorescence differential image signals for one sheet. To cope with this, the third embodiment makes it possible to generate a fluorescence differential image signal with the capsule endoscope system by applying the first embodiment that makes it possible to generate a fluorescence differential image signal for one sheet merely by using an image signal of one frame.

Similarly to the first embodiment, in a case where there are findings obtained beforehand by actual measurement, or the like, in the third embodiment, it is possible to set the order of function to be used for approximation in the approximate expression $L_e$. Accordingly, in this case, the estimation unit 33f can estimate the image signal of the middle G pixel as long as there is any one of the image signals of the B pixel and the R pixel.

Fourth Embodiment

Next, a fourth embodiment will be described. In the fourth embodiment, reference will be made to an example in which the second embodiment is applied to a capsule endoscope system.

Figure 23:
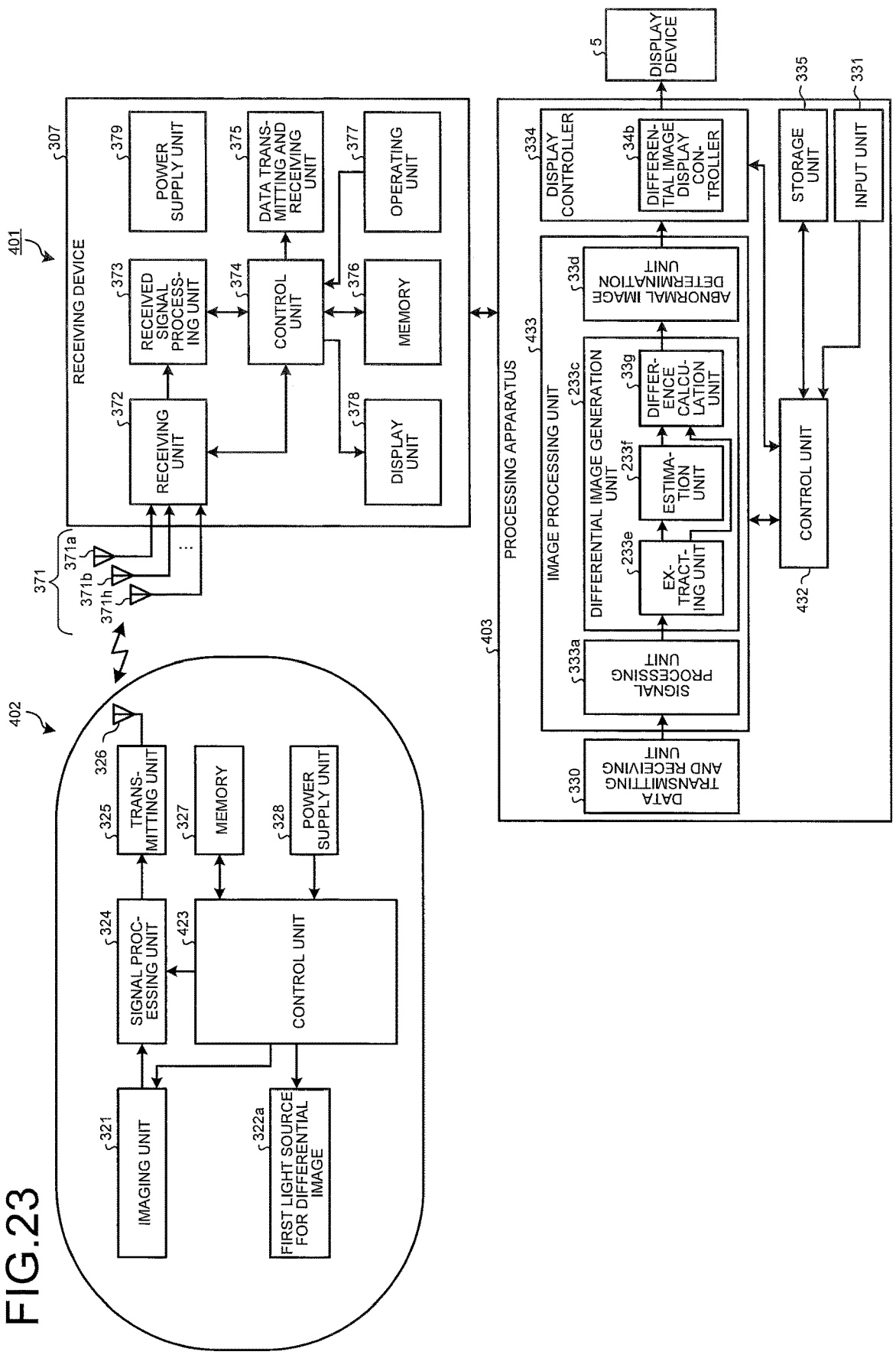
FIG. 23 is a block diagram illustrating a configuration of a capsule endoscope system according to a fourth embodiment.

FIG. 23 is a block diagram illustrating a configuration of a capsule endoscope system according to the fourth embodiment. As illustrated in FIG. 23, a capsule endoscope system 401 according to the fourth embodiment has a capsule endoscope 402 in place of the capsule endoscope 302 in FIG. 22, and has a processing apparatus 403 in place of the processing apparatus 303.

The capsule endoscope 402 includes a first light source 322a for a differential image, as a light source. Accordingly, similarly to the second embodiment, the capsule endoscope 402 emits solely the light $E_b$, namely, the fluorescence excitation light as the light of the first wavelength band, which is the light for a fluorescence differential image. As described in the second embodiment, a biological tissue as an object emits autofluorescence F when irradiated with the light $E_b$. The autofluorescence F includes autofluorescence $F_g$ having a wavelength of 500 nm to 600 nm (peak wavelength as the first peak wavelength: wavelength 510 nm) and autofluorescence $F_r$ having a wavelength of 650 nm to 800 nm at deep portion of mucosa (peak wavelength as the second peak wavelength: wavelength 660 nm). The G pixel of the imaging unit 321 receives the autofluorescence $F_g$, and the R pixel receives the autofluorescence $F_r$. The B pixel of the imaging unit 321 receives reflected light $R_b$ of the light $E_b$. A control unit 423 has functions similar to the functions of the control unit 323.

The processing apparatus 403 includes an image processing unit 433 in place of the image processing unit 333 illustrated in FIG. 22. The image processing unit 433 includes the differential image generation unit 233c having the extracting unit 233e, the estimation unit 233f, and the difference calculation unit 33g. A control unit 432 has functions similar to the functions of the control unit 332. The image signal as a processing target, input from the data transmitting and receiving unit 330 is an image signal captured by the imaging unit 321 of the capsule endoscope 402. The image signal of one frame includes the image signal (second image signal) generated by the G pixel that has received autofluorescence $F_g$ having a wavelength of 500 nm to 600 nm among the autofluorescence in response to the light $E_b$, the image signal (first image signal) generated by the B pixel that has received the reflected light $R_b$ of the light $E_b$, and the image signal (third image signal) generated by the R pixel that has received the autofluorescence $F_r$ generated from the deep portion of the biological tissue (mucosal tissue) having a predetermined uniformity. Accordingly, the differential image generation unit 233c generates a fluorescence differential image by performing processing similar to the processing of generating a fluorescence differential image (refer to FIG. 18) executed by the differential image generation unit 233c in the second embodiment.

According to the fourth embodiment, it is possible to achieve an effect similar to the second embodiment. In addition, it would be sufficient to use merely the first light source for a differential image that emits a wavelength of 390 nm to 470 nm as fluorescence excitation light, as the light source needed for generating fluorescence differential image. Accordingly, it is possible to simplify configuration of the capsule endoscope 402 compared with the third embodiment.

In addition, similarly to the second embodiment, in a case where there are findings obtained beforehand by actual measurement, or the like, in the fourth embodiment, it is possible to set the order of function to be used for approximation in the approximate expression $L_f$. Accordingly, in this case, the estimation unit 233f can estimate the image signal of the middle G pixel as long as there is any one of the image signals of the B pixel and the R pixel.

It is also allowable to configure such that the differential image generation units 33c and 233c and the abnormal image determination unit 33d illustrated in FIGS. 22 and 23 are provided in the received signal processing unit 373 of the receiving device 307 instead of the image processing units 333 and 433 of the processing apparatuses 303 and 403. Accordingly, it is allowable to configure such that the receiving device 307 can generate the fluorescence differential image signal.

The running programs for individual processing to be executed in the image processing units 33, 233, 333, and 433 and in other units, according to the present embodiment, may be recorded on a computer readable recording medium such as a CD-ROM, a flexible disk, a CD-R and a DVD in a form of a file that can be installed or executed, and may be provided. Alternatively, the program may be stored on a computer connected to a network such as the Internet and may be supplied by downloading the program via the network. It is also allowable to provide or distribute the program via a network including the Internet.

According to some embodiments, a first image signal that is an image signal generated by a pixel that has received light of a first wavelength band and a second image signal that is an image signal generated by a pixel that has received light of a second wavelength band are individually extracted from the image signal of one frame. Subsequently, an image signal to be generated by a pixel that has received the light of the second wavelength band is estimated by the extracted first image signal, and then, a differential image signal is obtained by calculating a difference, on a corresponding image portion, between the extracted second image signal and the estimated image signal. With this configuration, it is possible to generate a differential image signal for one sheet by using merely an image signal of one frame and thus to efficiently generate a differential image that highlights an abnormal site.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing apparatus comprising:
a processor comprising hardware, wherein the processor is configured to:
extract, from an image signal of one frame, a first image signal corresponding to light, received by a first pixel, from an object irradiated by light of a first wavelength band;
extract, from the image signal of the one frame, a second image signal corresponding to fluorescence, received by a second pixel, from the object irradiated by the light of the first wavelength band;
estimate a reference image signal corresponding to light without the fluorescence, estimated to be received by the second pixel, from the object irradiated by the light of the first wavelength band, wherein the reference image signal is estimated by applying an approximate expression to the first image signal; and
calculate a difference, between the second image signal and the reference image signal, thereby to obtain a differential image signal.

2. The processing apparatus according to claim 1, wherein the first wavelength band falls within a wavelength range of 390 nm to 470 nm, and
wherein the processor is configured to:
extract, from the image signal of the one frame, a third image signal corresponding to light, received by a third pixel, from the object irradiated by light of a third a wavelength band of 650 nm to 800 nm; and
estimate the reference image signal by applying an approximate expression to the first image signal and the third image signal.

3. The processing apparatus according to claim 1, wherein the processor is configured to generate, from the differential image signal, a signal of an abnormal image that contains a portion of the one frame having a value of the difference which exceeds a predetermined value.

4. The processing apparatus according to claim 1, wherein the processor is configured to generate, from the differential image signal, a differential image display image signal for displaying a portion of the one frame having a value of the difference which exceeds a predetermined value, in a color distinguishable from another portion of the one frame.

5. The processing apparatus according to claim 1, wherein the difference is a difference in intensity between the second image signal and the reference image signal.

6. An endoscope system comprising:
a light source configured to emit light of a first wavelength band to an object;
an image sensor configured to receive light from the object irradiated with the light of the first wavelength band to generate an image signal of one frame; and
a processor comprising hardware, wherein the processor is configured to:
extract, from the image signal of the one frame, a first image signal corresponding to the light, received by a first pixel from the object irradiated by the light of the first wavelength band;
extract, from the image signal of the one frame, a second image signal corresponding to fluorescence, received by a second pixel, from the object irradiated by the light of the first wavelength band;
estimate a reference image signal corresponding to light without the fluorescence, estimated to be received by the second pixel, from the object irradiated by the light of the first wavelength band, wherein the reference image signal is estimated by applying an approximate expression to the first image signal; and
calculate a difference, between the second image signal and the reference image signal, thereby to obtain a differential image signal.

7. The endoscope system according to claim 6, wherein the first wavelength band falls within a wavelength range of 390 nm to 470 nm,
wherein the light source is configured to emit a light of a third wavelength band of 650 nm to 800 nm, and
wherein the processor is configured to:
extract, from the image signal of the one frame, a third image signal corresponding to light, received by a third pixel of the image sensor, from the object irradiated by the light of the third wavelength band; and estimate the reference image signal by applying an approximate expression to the first image signal and the third image signal.

8. The endoscope system according to claim 6, wherein the processor is configured to generate, from the differential image signal, a signal of an abnormal image that contains a portion of the one frame having a value of the difference which exceeds a predetermined value.

9. The endoscope system according to claim 6, wherein the processor is configured to generate, from the differential image signal, a differential image display image signal for displaying a portion of the one frame having a value of the difference which exceeds a predetermined value, in a color distinguishable from another portion of the one frame.

10. The endoscope system according to claim 6, comprising:
an endoscope apparatus comprising the image sensor.

11. The endoscope system according to claim 6, comprising:
an endoscope apparatus comprises the light source, the image sensor, and a transmitter configured to wireless transmit the image signal generated by the image sensor, to outside,
wherein the processor is configured to process the image signal perform signal processing on the image signal wirelessly transmitted from the endoscope apparatus.

12. A method comprising:
extracting, from an image signal of one frame, a first image signal corresponding to light, received by a first pixel, from an object irradiated by light of a first wavelength band;
extracting, from the image signal of the one frame, a second image signal corresponding to fluorescence, received by a second pixel, from the object irradiated by the light of the first wavelength band;
estimating a reference image signal corresponding to light without the fluorescence, estimated to be received by the second pixel, from the object irradiated by the light of the first wavelength band, wherein the reference image signal is estimated by applying an approximate expression to the first image signal; and
calculating a difference between the second image signal and the reference image signal, thereby to obtain a differential image signal.

13. A non-transitory computer-readable recording medium with an executable program stored thereon, the program causing a computer to at least execute:
extracting, from an image signal of one frame, a first image signal corresponding to light, received by a first pixel, from an object irradiated by light of a first wavelength band;
extracting, from the image signal of the one frame, a second image signal corresponding to fluorescence, received by a second pixel, from the object irradiated by the light of the first wavelength band;
estimating a reference image signal corresponding to light without the fluorescence, estimated to be received by the second pixel, from the object irradiated by the light of the first wavelength band, wherein the reference image signal is estimated by applying an approximate expression to the first image signal; and
calculating a difference between the second image signal and the reference image signal, thereby to obtain a differential image signal.

* * * * *